(12) United States Patent
Soerens et al.

(10) Patent No.: US 7,619,131 B2
(45) Date of Patent: Nov. 17, 2009

(54) ARTICLES COMPRISING TRANSPARENT/TRANSLUCENT POLYMER COMPOSITION

(75) Inventors: Dave Allen Soerens, Neenah, WI (US);
Angela Jones Lang, High Point, NC (US); Iqbal Ahmed, Greensboro, NC (US); Scott J. Smith, Greensboro, NC (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 390 days.

(21) Appl. No.: 11/292,570

(22) Filed: Dec. 2, 2005

(65) Prior Publication Data

US 2007/0129696 A1    Jun. 7, 2007

(51) Int. Cl.
*A61F 13/15*     (2006.01)
*C08F 4/04*      (2006.01)
*C08F 30/08*     (2006.01)
*C08F 118/02*    (2006.01)

(52) U.S. Cl. ........................ 604/366; 604/375; 604/368; 604/367; 526/218.1; 526/319; 526/279

(58) Field of Classification Search .................. 604/366, 604/375, 368, 367; 526/218.1, 319, 279, 526/317.1
See application file for complete search history.

(56) References Cited

U.S. PATENT DOCUMENTS

| 3,617,362 A | 11/1971 | Bemmels et al. |
| 3,647,415 A | 3/1972 | Yano et al. |
| 3,802,817 A | 4/1974 | Matsuki et al. |
| 3,951,893 A | 4/1976 | Gander |
| 3,959,242 A | 5/1976 | Watts et al. |
| 3,963,605 A | 6/1976 | Seabourn |
| 3,963,805 A | 6/1976 | Chu |
| 4,251,643 A | 2/1981 | Harada et al. |

(Continued)

FOREIGN PATENT DOCUMENTS

CA           756190          4/1967

(Continued)

OTHER PUBLICATIONS

Brunauer, Stephen et al., "Adsorption of Gases in Multimolecular Layers," *The Journal of the American Chemical Society*, vol. LX, Jan.-Jun. 1938, pp. 309-319.

(Continued)

*Primary Examiner*—Jacqueline F. Stephens
(74) *Attorney, Agent, or Firm*—Bryan R. Rosiejka

(57) ABSTRACT

The present invention provides a translucent absorbent composite having a substrate with a light transmittance of at least about 60% and a flexible superabsorbent binder polymer composition applied to the substrate. The polymer composition may be prepared from the reaction product of a monomer solution including at least 15% by mass monoethylenically unsaturated monomer selected from carboxylic acid, carboxylic acid salts, sulphonic acid, sulphonic acid salts, phosphoric acid, or phosphoric acid salts; an acrylate or methacrylate ester that contains an alkoxysilane functionality; a copolymerizable hydrophilic glycol containing an ester monomer; an initiator system; and a neutralizing agent. The unsaturated monomer is neutralized to at least 25 mol % and the flexible superabsorbent binder polymer composition has a residual monoethylenically unsaturated monomer content of less than about 1000 ppm. The absorbent composite has a light transmittance of at least 45%. Also provided are absorbent articles containing the absorbent composite.

15 Claims, 7 Drawing Sheets

U.S. PATENT DOCUMENTS

| | | | |
|---|---|---|---|
| 4,285,343 A | 8/1981 | McNair | |
| 4,291,136 A | 9/1981 | Keogh | |
| 4,328,323 A | 5/1982 | Keogh | |
| 4,343,917 A | 8/1982 | Keogh | |
| 4,353,997 A | 10/1982 | Keogh | |
| 4,369,289 A | 1/1983 | Keogh | |
| 4,375,448 A | 3/1983 | Appel et al. | |
| 4,408,011 A | 10/1983 | Barnabeo | |
| 4,434,272 A | 2/1984 | Keogh | |
| 4,440,907 A | 4/1984 | Keogh | |
| 4,446,279 A | 5/1984 | Keogh | |
| 4,459,396 A | 7/1984 | Yamasaki et al. | |
| 4,488,969 A | 12/1984 | Hou | |
| 4,489,029 A | 12/1984 | Keogh et al. | |
| 4,493,924 A | 1/1985 | Rifi | |
| 4,502,968 A | 3/1985 | Noda et al. | |
| 4,526,930 A | 7/1985 | Keogh | |
| 4,551,504 A | 11/1985 | Barnabeo | |
| 4,575,535 A | 3/1986 | Keogh | |
| 4,579,913 A | 4/1986 | Keogh | |
| 4,589,876 A | 5/1986 | Van Tilburg | |
| 4,593,071 A | 6/1986 | Keogh | |
| 4,608,047 A | 8/1986 | Mattingly | |
| 4,666,647 A | 5/1987 | Enloe et al. | |
| 4,676,820 A | 6/1987 | Le Sergent et al. | |
| 4,687,478 A | 8/1987 | Van Tillburg | |
| 4,704,116 A | 11/1987 | Enloe | |
| 4,753,993 A | 6/1988 | Keogh | |
| 4,761,258 A | 8/1988 | Enloe | |
| 4,767,820 A | 8/1988 | Keogh | |
| 4,798,603 A | 1/1989 | Meyer et al. | |
| 4,806,594 A | 2/1989 | Gross et al. | |
| 4,886,512 A | 12/1989 | Damico et al. | |
| 4,921,136 A | 5/1990 | Roggenburg, Jr. | |
| 4,940,646 A | 7/1990 | Pawlowski | |
| 4,950,264 A | 8/1990 | Osborn, III | |
| 5,009,653 A | 4/1991 | Osborn, III | |
| 5,047,282 A * | 9/1991 | Mier | 428/204 |
| 5,047,476 A | 9/1991 | Keogh | |
| 5,085,654 A | 2/1992 | Buell | |
| 5,089,564 A | 2/1992 | Bullen | |
| 5,112,919 A | 5/1992 | Furrer et al. | |
| 5,145,906 A | 9/1992 | Chambers et al. | |
| 5,176,668 A | 1/1993 | Bernardin | |
| 5,176,672 A | 1/1993 | Bruemmer et al. | |
| 5,190,563 A | 3/1993 | Herron et al. | |
| 5,192,606 A | 3/1993 | Proxmire et al. | |
| 5,196,470 A | 3/1993 | Anderson et al. | |
| 5,197,959 A | 3/1993 | Buell | |
| 5,204,404 A | 4/1993 | Werner, Jr. et al. | |
| 5,267,992 A | 12/1993 | Van Tilburg | |
| 5,284,703 A | 2/1994 | Everhart et al. | |
| 5,308,346 A | 5/1994 | Sneller et al. | |
| 5,342,342 A | 8/1994 | Kitaoka | |
| 5,354,829 A | 10/1994 | Swisher et al. | |
| 5,364,382 A | 11/1994 | Latimer et al. | |
| 5,389,728 A | 2/1995 | Prejean | |
| 5,407,600 A | 4/1995 | Ando et al. | |
| 5,427,844 A | 6/1995 | Murai et al. | |
| 5,429,628 A | 7/1995 | Trinh et al. | |
| 5,486,166 A | 1/1996 | Bishop et al. | |
| 5,490,846 A | 2/1996 | Ellis et al. | |
| 5,509,914 A | 4/1996 | Osborn, III | |
| 5,509,915 A | 4/1996 | Hanson et al. | |
| 5,532,350 A | 7/1996 | Cottrell et al. | |
| 5,543,215 A | 8/1996 | Hansen et al. | |
| 5,558,659 A | 9/1996 | Sherrod et al. | |
| 5,569,234 A | 10/1996 | Buell et al. | |
| 5,634,916 A | 6/1997 | Lavon et al. | |
| 5,649,916 A | 7/1997 | Dipalma et al. | |
| 5,656,132 A | 8/1997 | Farrington, Jr. et al. | |
| 5,702,378 A | 12/1997 | Widlund et al. | |
| 5,716,349 A | 2/1998 | Taylor et al. | |
| 5,733,570 A | 3/1998 | Chen et al. | |
| 5,853,867 A | 12/1998 | Harada et al. | |
| 5,859,074 A | 1/1999 | Rezai et al. | |
| 5,911,937 A | 6/1999 | Hekal | |
| 5,932,668 A | 8/1999 | Friebe et al. | |
| 5,945,476 A | 8/1999 | Roesler et al. | |
| 5,961,763 A | 10/1999 | Makoui et al. | |
| 6,013,855 A | 1/2000 | McPherson et al. | |
| 6,020,071 A | 2/2000 | Watson | |
| 6,020,171 A | 2/2000 | Saito et al. | |
| 6,054,523 A | 4/2000 | Braun et al. | |
| 6,110,158 A | 8/2000 | Kielpikowski | |
| 6,110,533 A | 8/2000 | Cote et al. | |
| 6,149,934 A | 11/2000 | Krzysik et al. | |
| 6,183,872 B1 | 2/2001 | Tanaka et al. | |
| 6,200,684 B1 | 3/2001 | Yamaguchi et al. | |
| 6,214,274 B1 | 4/2001 | Melius et al. | |
| 6,229,062 B1 | 5/2001 | Mandell et al. | |
| 6,315,765 B1 | 11/2001 | Datta et al. | |
| 6,330,735 B1 | 12/2001 | Hahn et al. | |
| 6,369,290 B1 | 4/2002 | Glaug et al. | |
| 6,376,741 B1 | 4/2002 | Guarracino et al. | |
| 6,387,084 B1 | 5/2002 | VanGompel et al. | |
| 6,403,857 B1 | 6/2002 | Gross et al. | |
| 6,417,425 B1 | 7/2002 | Whitmore et al. | |
| 6,425,979 B1 | 7/2002 | Hansen et al. | |
| 6,458,877 B1 | 10/2002 | Ahmed et al. | |
| 6,464,675 B2 | 10/2002 | De Carvalho | |
| 6,497,690 B2 | 12/2002 | Haarer | |
| 6,511,465 B1 | 1/2003 | Freiburger et al. | |
| 6,534,572 B1 | 3/2003 | Ahmed et al. | |
| 6,576,809 B1 * | 6/2003 | Inoue et al. | 604/361 |
| 6,582,413 B2 | 6/2003 | Krautkramer et al. | |
| 6,596,402 B2 | 7/2003 | Soerens et al. | |
| 6,663,611 B2 | 12/2003 | Blaney et al. | |
| 6,706,945 B1 | 3/2004 | Melius et al. | |
| 6,737,491 B2 | 5/2004 | Soerens et al. | |
| 6,790,519 B1 | 9/2004 | Johnson et al. | |
| 6,808,801 B2 | 10/2004 | George et al. | |
| 6,822,135 B2 | 11/2004 | Soerens et al. | |
| 6,849,685 B2 | 2/2005 | Soerens et al. | |
| 6,887,961 B2 | 5/2005 | Soerens et al. | |
| 6,888,044 B2 | 5/2005 | Fell et al. | |
| 6,964,803 B2 | 11/2005 | Krautkramer et al. | |
| 7,115,321 B2 | 10/2006 | Soerens et al. | |
| 2002/0049417 A1 | 4/2002 | Onishi et al. | |
| 2002/0090453 A1 | 7/2002 | Muthiah et al. | |
| 2003/0008989 A1 | 1/2003 | Gore et al. | |
| 2003/0065299 A1 * | 4/2003 | Carlucci et al. | 604/385.01 |
| 2003/0100875 A1 | 5/2003 | Suekane et al. | |
| 2003/0120253 A1 | 6/2003 | Wentzel et al. | |
| 2003/0149413 A1 | 8/2003 | Mehawej | |
| 2004/0019168 A1 * | 1/2004 | Soerens et al. | 526/271 |
| 2004/0019339 A1 | 1/2004 | Ranganathan et al. | |
| 2004/0024092 A1 | 2/2004 | Soerens et al. | |
| 2004/0043688 A1 | 3/2004 | Soerens et al. | |
| 2004/0060112 A1 | 4/2004 | Fell et al. | |
| 2004/0106721 A1 | 6/2004 | Soerens | |
| 2004/0116014 A1 | 6/2004 | Soerens et al. | |
| 2004/0116885 A1 | 6/2004 | Soerens et al. | |
| 2004/0120921 A1 | 6/2004 | Quincy et al. | |
| 2004/0122387 A1 | 6/2004 | Long et al. | |
| 2004/0122390 A1 | 6/2004 | Soerens et al. | |
| 2004/0157971 A1 | 8/2004 | Kim | |
| 2004/0170813 A1 * | 9/2004 | Digiacomantonio et al. | 428/195.1 |
| 2004/0175556 A1 | 9/2004 | Clark et al. | |
| 2005/0084412 A1 | 4/2005 | MacDonald et al. | |
| 2005/0084464 A1 | 4/2005 | McGrath et al. | |
| 2005/0084474 A1 | 4/2005 | Wu et al. | |
| 2005/0085144 A1 | 4/2005 | MacDonald et al. | |

| | | | |
|---|---|---|---|
| 2005/0131363 A1 | 6/2005 | MacDonald et al. | |
| 2005/0194559 A1 | 9/2005 | Lewandowski et al. | |
| 2006/0105963 A1 | 5/2006 | Yang et al. | |
| 2006/0142712 A1 | 6/2006 | Quincy | |

FOREIGN PATENT DOCUMENTS

| | | |
|---|---|---|
| DE | 100 17 446 A1 | 11/2001 |
| EP | 0 132 910 A2 | 2/1985 |
| EP | 0 348 978 A2 | 1/1990 |
| EP | 0 475 664 A1 | 3/1992 |
| EP | 0 705 861 A1 | 4/1996 |
| EP | 0 844 265 A1 | 5/1998 |
| EP | 0 992 252 A2 | 4/2000 |
| EP | 1 013 291 A1 | 6/2000 |
| EP | 1 059 320 A2 | 12/2000 |
| EP | 1 138 293 A1 | 10/2001 |
| EP | 1 149 594 A1 | 10/2001 |
| EP | 1 149 595 A1 | 10/2001 |
| EP | 1 188 854 A1 | 3/2002 |
| EP | 1 199 059 A1 | 4/2002 |
| EP | 1 216 676 A2 | 6/2002 |
| EP | 1 275 404 A1 | 1/2003 |
| EP | 1 402 905 A1 | 3/2004 |
| EP | 1 529 508 A2 | 5/2005 |
| JP | 02-006659 A | 1/1990 |
| JP | 09-030944 A | 2/1997 |
| WO | WO 98/26808 A2 | 6/1998 |
| WO | WO 99/00093 A1 | 1/1999 |
| WO | WO 99/57201 A1 | 11/1999 |
| WO | WO 99/63925 A1 | 12/1999 |
| WO | WO 99/64083 A1 | 12/1999 |
| WO | WO 00/59556 A2 | 10/2000 |
| WO | WO 01/32226 A1 | 5/2001 |
| WO | WO 02/20067 A2 | 3/2002 |
| WO | WO 02/53664 A2 | 7/2002 |
| WO | WO 02/95112 A1 | 11/2002 |
| WO | WO 03/020193 A1 | 3/2003 |
| WO | WO 03/086493 A1 | 10/2003 |

OTHER PUBLICATIONS

Sato, Hiroshi et al., "Analysis of Malodorous Volatile Substances of Human Waste: Feces and Urine," *Journal of Health Science*, vol. 47, No. 5, 2001, pp. 483-490.

American Society for Testing Materials (ASTM) Designation: D1003-00, "Standard Test Method for Haze and Luminous Transmittance of Transparent Plastics," pp. 1-6, published Jul. 2000.

Neumann, A.W., and R.J. Good, "Techniques of Measuring Contact Angles," Chapter 2, *Surface and Colloid Science—Experimental Methods*, vol. 11, edited by R.J. Good and R.R. Stromberg, Plenum Press, 1979, pp. 31-91.

* cited by examiner

ARTICLES COMPRISING TRANSPARENT/TRANSLUCENT POLYMER COMPOSITION

BACKGROUND

Articles are an essential part of people's lives. For example, absorbent articles can be useful for absorbing many types of fluids, including fluids secreted or eliminated by the human body. Superabsorbent materials are frequently used in absorbent articles to help improve the absorbent properties of such articles. Superabsorbent materials are generally polymer based and are available in many forms, such as powders, granules, microparticles, films and fibers, for example. Upon contact with fluids, such superabsorbent materials swell by absorbing the fluids into their structures. In general, superabsorbent materials can quickly absorb fluids insulted into such articles, and can retain such fluids to prevent leakage and help provide a dry feel even after fluid insult.

Absorbent articles are typically white or are colored to a desired color depending on the manufacturer and/or the intended end use. Color is generally imparted with pigments, fillers or dyes which are added to the raw materials used to make the absorbent article. Color has been historically used in absorbent articles to communicate a hygienic condition of the article prior to use. Typically, a white color has been used as the predominate color of absorbent articles to convey that the absorbent articles are of a hygienic condition.

Current fashion trends have resulted in undergarments having colors other than the traditional white. In addition, these current fashion trends have yielded outer clothing which has a certain "see-through" quality, such that the color of the undergarments can be easily recognized through the outer clothing. By having absorbent articles, such as pantiliners and sanitary napkins, with a white color and the undergarments of a different color, the white color may make the absorbent article or the contour of the absorbent article visible through the undergarment and outer clothing, resulting in a lack of discretion for the user of the absorbent article.

In addition, coloring the absorbent article to match the coloring of the undergarments would be a possible option to provide discretion. However, preparing absorbent articles that will match or nearly match the color of the wide variety of undergarments currently being manufactured by the clothing industry would be a nearly impossible task for a manufacturer of absorbent articles. For each product line, the manufacturer of absorbent articles would need to provide various colors of absorbent articles. In addition, having many different colors would result in many different product codes that a retailer would need to stock on its shelves. With shelf space at a premium in today's retail market, providing sufficient shelf space for a given manufacturer to display its products would or could require more than twice the shelf space currently available. Furthermore, simple changes in a dye lot for the absorbent articles or the undergarments could result in absorbent articles that would not match or nearly match the undergarments. Currently available absorbent articles typically do not blend in with the surrounding use environments; thereby providing little, if any, discretion to the user due to color of the articles. Therefore, there is a need in the art for absorbent articles which are transparent or translucent so that the absorbent articles will blend in with the use environments and can be discretely used by a user without others readily determining that the user is using an absorbent article.

In addition, there is continuing effort to improve the performance of such articles. One desire is to make absorbent articles thinner. Another desire is to make absorbent articles more flexible. Still another desire is to increase the integrity of absorbent articles, in both a wet and dry condition. Yet another desire is to improve or maintain the absorbent intake and/or the absorbent capacity of such articles. One method for improving absorbent properties could be to increase the amount of superabsorbent material in the article. However, an increase in superabsorbent material content can increase the thickness of the article and the shake-out of superabsorbent absorbent material, and likewise can decrease the flexibility and/or the integrity of the article. Accordingly, there is a need for transparent or translucent absorbent articles which achieve desired absorbent properties while maintaining desired thinness and/or flexibility and/or integrity in both a wet and dry condition.

SUMMARY OF THE INVENTION

In response to the needs described above, the present invention provides a thin, flexible, translucent or nearly transparent absorbent composite. The absorbent composite of the present invention may be used in an absorbent article, providing an absorbent article that will blend with the use environment of the absorbent article, and will provide sufficient capacity for a given absorption task. In the present invention, the absorbent composite has a substrate and an absorbent material applied to the substrate. The absorbent material contains a flexible superabsorbent binder polymer composition prepared from the reaction product of a monomer solution including at least 15% by mass monoethylenically unsaturated monomer selected from carboxylic acid, carboxylic acid salts, sulphonic acid, sulphonic acid salts, phosphoric acid, or phosphoric acid salts; an acrylate or methacrylate ester that contains an alkoxysilane functionality; a copolymerizable hydrophilic glycol containing an ester monomer; an initiator system; and a neutralizing agent. In some aspects, the unsaturated monomer is neutralized to at least 25 mol %. In other aspects, the flexible superabsorbent binder polymer composition has a residual monoethylenically unsaturated monomer content of less than about 1000 ppm. The absorbent composite in the absorbent area has a light transmittance of at least 45%. In one embodiment of the present invention, the absorbent composite may have a light transmission of at least 60%.

In another embodiment of the present invention, the absorbent composite has at least one additional layer. In this embodiment of the present invention, an additional layer is adjacent the substrate with the absorbent material applied to the substrate. The additional layer may be selected to impart different properties to the absorbent composite including as a fluid intake layer or as a fluid impermeable layer. More than one additional layer may be present in the absorbent composite of the present invention. In a further aspect of this embodiment of the present invention, the additional layer may have a light transmittance of at least 60%.

In still another embodiment of the present invention, two additional layers are present in the absorbent composite. When two additional layers are present in the composite, the substrate and absorbent material applied thereto may be a top or intermediate layer of the composite. In this regard, one configuration of the composite has the substrate with the absorbent material applied thereto positioned between the first and second additional layers. In a further embodiment of this aspect of the invention, each of the first and second layers may have a light transmittance of at least 60%.

In yet another embodiment of the present invention, provided is a translucent absorbent composite having a backing, and an absorbent layer, where the absorbent layer is positioned adjacent the backing layer, and the absorbent layer contains a substrate and an absorbent material applied to the substrate. The absorbent material contains a flexible superabsorbent binder polymer composition prepared from the reaction product of a monomer solution including at least 15% by mass monoethylenically unsaturated monomer selected from carboxylic acid, carboxylic acid salts, sulphonic acid, sulphonic acid salts, phosphoric acid, or phosphoric acid salts; an acrylate or methacrylate ester that contains an alkoxysilane functionality; a copolymerizable hydrophilic glycol containing an ester monomer; an initiator system; and a neutralizing agent. In some aspects, the unsaturated monomer is neutralized to at least 25 mol %. In other aspects, the flexible superabsorbent binder polymer composition has a residual monoethylenically unsaturated monomer content of less than about 1000 ppm. In some aspects, the absorbent layer has a light transmittance of at least 45%. In further aspects, the backing layer has a light transmittance of at least 60%, and the overall absorbent composite has a minimum light transmittance of at least 45%. In yet another aspect of this embodiment, the absorbent composite may have a perimeter region and a central region. The backing layer is present in both the perimeter region and the central region, and the absorbent layer is positioned adjacent the backing layer and is only present in the central region of the absorbent composite. In yet a further aspect of this embodiment of the present invention, the perimeter region may have a light transmittance of at least 60% and the central region may have a light transmittance of at least 45%. The absorbent composite of this aspect of the present invention may also have a liner layer, where the absorbent layer is positioned between the liner layer and the backing layer. The liner layer also has a light transmittance of at least 60%.

Also provided by the present invention is an absorbent article prepared from the absorbent composite. In this embodiment, an absorbent article of the present invention has a backing layer, an absorbent layer and a bodyside liner. The absorbent layer is positioned between the bodyside liner and the backing layer, the absorbent layer has a substrate and an absorbent material applied to the substrate. The absorbent material contains a flexible superabsorbent binder polymer composition prepared from the reaction product of a monomer solution including at least 15% by mass monoethylenically unsaturated monomer selected from carboxylic acid, carboxylic acid salts, sulphonic acid, sulphonic acid salts, phosphoric acid, or phosphoric acid salts; an acrylate or methacrylate ester that contains an alkoxysilane functionality; a copolymerizable hydrophilic glycol containing an ester monomer; an initiator system; and a neutralizing agent. In some aspects, the unsaturated monomer is neutralized to at least 25 mol %. In other aspects, the flexible superabsorbent binder polymer composition has a residual monoethylenically unsaturated monomer content of less than about 1000 ppm. The absorbent layer of the absorbent article has a light transmittance of at least 45% and the backing layer and the bodyside liner each have a light transmittance of at least 60%. The absorbent article of this aspect of the present invention has a minimum light transmittance of at least 45%.

In yet another embodiment of the present invention, the absorbent article has a perimeter region and a central region. The backing layer and the bodyside liner are each present in both the perimeter region and the central region, and the absorbent layer is positioned between the backing layer and the bodyside liner layer. The absorbent layer is only present in the central region of the absorbent article. In yet a further aspect of this embodiment of the present invention, the perimeter region may have a light transmittance of at least 60% and the central region may have a light transmittance of at least 45%. In another aspect of this embodiment of the present invention, the perimeter region of the absorbent article has a light transmittance of at least 80% and the central region of the absorbent article has a light transmittance of between about 55% and about 79%. Absorbent articles of the present invention include, but are not limited to, a sanitary napkin, an incontinence pad, a pantiliner, a bandage, a bed pad or a furniture pad.

In a further embodiment of the present invention, the present invention also provides an absorbent article comprising a body contacting surface, a surface opposed the body contacting surface, an absorbent core positioned between the body contacting surface and the surface opposed the body contacting surface, and longitudinal edges extending along an edge of absorbent core and flaps. The flaps extend from the longitudinal edges of the absorbent article and the flaps contain an absorbent material, which is capable of absorbing fluids. The flaps have a light transmittance of at least 45%.

Also provided by the present invention is an absorbent article having a backing layer, an absorbent layer and optionally a bodyside liner. The absorbent layer is positioned between the optional bodyside liner and the backing layer, the absorbent layer has a substrate and an absorbent material applied to the substrate. The absorbent material contains a flexible superabsorbent binder polymer composition prepared from the reaction product of a monomer solution including at least 15% by mass monoethylenically unsaturated monomer selected from carboxylic acid, carboxylic acid salts, sulphonic acid, sulphonic acid salts, phosphoric acid, or phosphoric acid salts; a plasticizer; an acrylate or methacrylate ester that contains an alkoxysilane functionality; an initiator system; and a neutralizing agent. In some aspects, the flexible superabsorbent binder polymer composition has a residual monoethylenically unsaturated monomer content of less than about 1000 ppm. The absorbent layer of the absorbent article has a light transmittance of at least 45% and the backing layer and the optional bodyside liner each have a light transmittance of at least 60%. The backing layer and the optional bodyside liner each may be present in both the perimeter region and the central region, and the absorbent layer is positioned between the backing layer and the optional bodyside liner layer. The absorbent layer is only present in the central region of the absorbent article. In yet a further aspect of this embodiment of the present invention, the perimeter region may have a light transmittance of at least 60% and the central region may have a light transmittance of at least 45%. In another aspect of this embodiment of the present invention, the perimeter region of the absorbent article has a light transmittance of at least 80% and the central region of the absorbent article has a light transmittance of between about 55% and about 79%. In some aspects of this embodiment, the absorbent composite can have an overall thickness of between about 0.25 mm to about 5.0 mm, such as between about 0.25 mm to about 1.5 mm.

Also provided by the present invention is an absorbent article having a backing layer, an absorbent layer and optionally a bodyside liner. The absorbent layer is positioned between the optional bodyside liner and the backing layer, the absorbent layer has a substrate and an absorbent material applied to the substrate. The absorbent material contains a flexible superabsorbent binder polymer composition prepared from the reaction product of a monomer solution including at least 15% by mass monoethylenically unsaturated monomer selected from carboxylic acid, carboxylic acid salts, sulphonic acid, sulphonic acid salts, phosphoric acid, or phosphoric acid salts; a plasticizer; an acrylate or methacrylate ester that contains an alkoxysilane functionality; a chain transfer agent; a transition metal salt; an initiator system; and a neutralizing agent. In some aspects, the the flexible superabsorbent binder polymer composition has a weight average molecular weight of from about 100,000 to about 650,000 g/mole. In other aspects, the flexible superabsorbent binder polymer composition has a viscosity after 16 hours of less than about 10,000 cps. In yet other aspects, the flexible superabsorbent binder polymer composition has a residual monoethylenically unsaturated monomer content of less than about 1000 ppm. The absorbent layer of the absorbent article has a light transmittance of at least 45% and the backing layer and the optional bodyside liner each have a light transmittance of at least 60%. The backing layer and the optional bodyside liner each may be present in both the perimeter region and the central region, and the absorbent layer is positioned between the backing layer and the optional bodyside liner layer. The absorbent layer is only present in the central region of the absorbent article. In yet a further aspect of this embodiment of the present invention, the perimeter region may have a light transmittance of at least 60% and the central region may have a light transmittance of at least 45%. In another aspect of this embodiment of the present invention, the perimeter region of the absorbent article has a light transmittance of at least 80% and the central region of the absorbent article has a light transmittance of between about 55% and about 79%. In some aspects of this embodiment, the absorbent composite can have an overall thickness of between about 0.25 mm to about 5.0 mm, such as between about 0.25 mm to about 1.5 mm.

The result is an article which exhibits improved performance as well as greater comfort and confidence among the user.

Numerous other features and advantages of the present invention will appear from the following description. In the description, reference is made to exemplary embodiments of the invention. Such embodiments do not represent the full scope of the invention. Reference should therefore be made to the claims herein for interpreting the full scope of the invention.

Figure 1A:
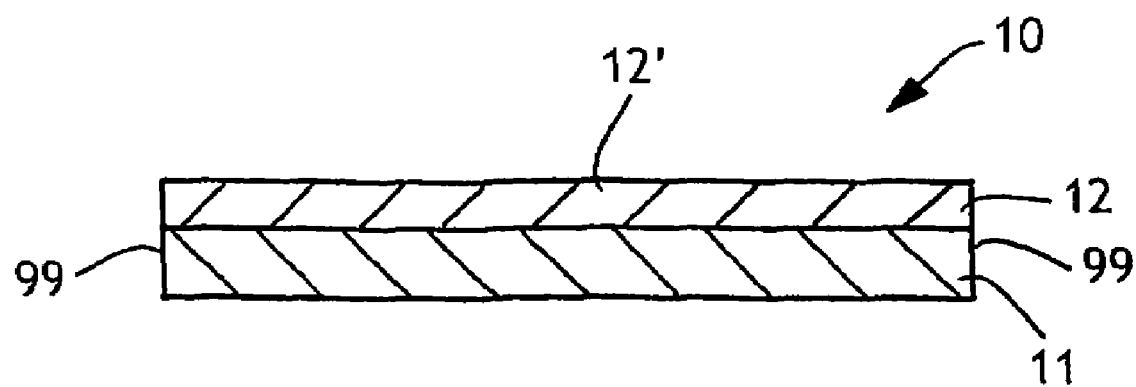
FIGS. 1A and 1B are each a cross-section of an absorbent composite of the present invention having a substrate layer and an absorbent layer.

Repeated use of reference characters in the present specification and drawings is intended to represent the same or analogous features or elements of the present invention.

DEFINITIONS

It should be noted that, when employed in the present disclosure, the terms "comprises," "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

The term "absorbent article" generally refers to devices which can absorb and contain fluids. For example, personal care absorbent articles refer to devices which are placed against or near the skin to absorb and contain the various fluids discharged from the body. The term "disposable" is used herein to describe absorbent articles that are not intended to be laundered or otherwise restored or reused as an absorbent article after a single use. Examples of such disposable absorbent articles include, but are not limited to, personal care absorbent articles, health/medical absorbent articles, and household/industrial absorbent articles.

The term "binder" includes materials that are capable of attaching themselves to a substrate or are capable of attaching other substances to a substrate.

The term "coform" is intended to describe a blend of meltblown fibers and cellulose fibers that is formed by air forming a meltblown polymer material while simultaneously blowing air-suspended cellulose fibers into the stream of meltblown fibers. The coform material may also include other materials, such as superabsorbent materials. The meltblown fibers containing wood fibers are collected on a forming surface, such as provided by a foraminous belt. The forming surface may include a gas-pervious material, such as spunbonded fabric material, that has been placed onto the forming surface.

As used herein, the term "connected" is intended to mean that two or more members are directly or indirectly connected to one another. When two or more members are directly connected to one another, it is meant that the two members are in direct contact with one another, without an intervening member or structure. When two or more members are indirectly connected to one another, it is meant that the two members are not in direct contact with one another, and may have an intervening member or structure between the two or more members connected to one another.

The term "fluid" refers to a substance in the form of a liquid or gas at room temperature and atmospheric pressure.

The term "fluid impermeable," when used to describe a layer or laminate, means that fluid such as water or bodily fluids will not pass substantially through the layer or laminate under ordinary use conditions in a direction generally perpendicular to the plane of the layer or laminate at the point of fluid contact.

The term "health/medical articles" includes a variety of professional and consumer health-care products including, but not limited to, products for applying hot or cold therapy, medical gowns (i.e., protective and/or surgical gowns), surgical drapes, caps, gloves, face masks, bandages, wound dressings, wipes, covers, containers, filters, disposable garments and bed pads, medical absorbent garments, underpads, and the like.

The term "household/industrial articles" include construction and packaging supplies, products for cleaning and disinfecting, wipes, covers, filters, towels, disposable cutting sheets, bath tissue, facial tissue, nonwoven roll goods, home-comfort products including pillows, pads, mats, cushions, masks and body care products such as products used to cleanse or treat the skin, laboratory coats, cover-alls, trash bags, stain removers, topical compositions, absorbent furniture liners or pads, pet care absorbent liners, laundry soil/ink absorbers, detergent agglomerators, lipophilic fluid separators, and the like.

The terms "hydrophilic" and "wettable" are used interchangeably to refer to a material having a contact angle of water in air of less than 90 degrees. The term "hydrophobic" refers to a material having a contact angle of water in air of at least 90 degrees. For the purposes of this application, contact angle measurements are determined as set forth in Robert J. Good and Robert J. Stromberg, Ed., in "Surface and Colloid Science—Experimental Methods," Vol. II, (Plenum Press, 1979), herein incorporated by reference in a manner consistent with the present disclosure.

The term "insult target zone" refers to an area of an absorbent composite where it is particularly desirable for the majority of a fluid insult, such as urine, menses, or bowel movement, to initially contact. In particular, for an absorbent composite with one or more fluid insult points in use, the insult target zone refers to the area of the absorbent composite extending a distance equal to 15% of the total length of the composite from each insult point in both directions.

The term "knife over roll coating" refers to a process in which a knife is positioned, with a specified gap, above a substrate that is moving beneath the knife on a moving roll. In this manner, the knife spreads a specified thickness of coating material onto the substrate.

The term "layer" when used in the singular can have the dual meaning of a single element or a plurality of elements.

The term "liquid impermeable" means a layer that is substantially impermeable or otherwise impermeable to liquids intended to be absorbed by the absorbent article.

The term "liquid permeable" means a layer that is operatively permeable to liquids intended to be absorbed by the absorbent article.

The term "materials" when used in the phrase "superabsorbent materials" refers generally to discrete units. The units can comprise particles, granules, fibers, flakes, agglomerates, rods, spheres, needles, particles coated with fibers or other additives, pulverized materials, powders, films, and the like, as well as combinations thereof. The materials can have any desired shape such as, for example, cubic, rod-like, polyhedral, spherical or semi-spherical, rounded or semi-rounded, angular, irregular, etc. Additionally, superabsorbent materials may be composed of more than one type of material.

The term "meltblown fibers" refers to fibers formed by extruding a molten thermoplastic material through a plurality of fine, usually circular, die capillaries as molten threads or filaments into a high velocity, usually heated, gas (e.g., air) stream which attenuates the filaments of molten thermoplastic material to reduce their diameter. Thereafter, the meltblown fibers are carried by the high velocity gas stream and are deposited on a collecting surface to form a web of randomly disbursed meltblown fibers.

The term "modifying agent" refers to a substance that may be added to a composition to modify the physical properties of the composition, such as the color or texture of the composition.

The terms "nonwoven" and "nonwoven web" refer to materials and webs of material having a structure of individual fibers or filaments which are interlaid, but not in an identifiable manner as in a knitted fabric. The terms "fiber" and "filament" are used herein interchangeably. Nonwoven fabrics or webs have been formed from many processes such as, for example, meltblowing processes, spunbonding processes, air laying processes, and bonded-carded-web processes. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91.)

The term "personal care absorbent articles" refers to any article used to control bodily fluids, and includes "absorbent products," which refers to any article configured to absorb and retain bodily exudates, including urine, bowel movements, blood and menses, and includes such a product in a packaged and unpackaged configuration. As such, "personal care articles" as used herein includes, but is not limited to, diapers, diaper pants, baby wipes, training pants, absorbent underpants, child care pants, swimwear, and other disposable garments; feminine care products including sanitary napkins, tissues, wipes, menstrual pads, menstrual pants, pantiliners, panty shields, interlabials, vaginal suppositories, tampons, and tampon applicators; adult-care products including wipes, pads such as breast pads, containers, incontinence products, and urinary shields; clothing components; bibs; athletic and recreation products; and the like.

The term "polymers" includes, but is not limited to, homopolymers, copolymers, such as for example, block, graft, random and alternating copolymers, terpolymers, etc. and blends and modifications thereof. Furthermore, unless otherwise specifically limited, the term "polymer" shall include all possible configurational isomers of the material. These configurations include, but are not limited to isotactic, syndiotactic and atactic symmetries.

The term "roll printing" or "roll coating" refers to a process in which the application of a deposited material, generally as a paste, onto a substrate is carried out by transferring the deposited material from a roll onto the substrate in a more or less uniform layer using one or more rolls, which may be engraved, and a pool cylinder. A doctor blade is used to scrape any excess deposited material from the rolls or substrate. The doctor blade may be flat or have a patterned edge such as slots or ridges.

The term "rotary screen printing" or "rotary screen coating" refers to a process that is a combination of roll printing or coating and screen printing or coating.

The term "screen printing" or "screen coating" refers to a method of applying a deposited material by forcing the material to be deposited through a screen that may have uniform openings or patterned openings.

The term "slot coating" refers to a process in which a slot die provides a thin, uniform coating on a substrate to be coated. In slot coating, the coating can be placed using an open gap in which the substrate to be coated is passed under the slot die, or a closed gap in which the slot die is aligned with a coating roll, such that there is a narrow gap or nip between the roller and slot die. The substrate to be coated is passed between the coating roll and the slot die.

The term "solution" when used in the phrase "flexible superabsorbent binder polymer solution," and derivatives thereof, refers to a polymer solution that has not yet been substantially crosslinked (i.e., a precursor), but will result in the flexible superabsorbent binder polymer composition once crosslinking occurs.

The term "spontaneous" crosslinking refers to crosslinking which occurs without radiation, catalysis, or any other inducement other than the specified temperature of not more than about 150° C., such as not more than about 120° C., or not more than about 100° C.

The terms "spunbond" and "spunbonded fiber" refer to fibers which are formed by extruding filaments of molten thermoplastic material from a plurality of fine, usually circular, capillaries of a spinneret, and then rapidly reducing the diameter of the extruded filaments.

The terms "superabsorbent" and "superabsorbent materials" refer to water-swellable, water-insoluble organic or inorganic materials capable, under the most favorable conditions, of absorbing at least about 10 times their weight, or at least about 15 times their weight, or at least about 25 times their weight in an aqueous solution containing 0.9 weight percent sodium chloride. In contrast, "absorbent materials" are capable, under the most favorable conditions, of absorbing at least 5 times their weight of an aqueous solution containing 0.9 weight percent sodium chloride.

The term "support layer" refers to a layer of the absorbent article in which the absorbent layer is formed.

The term "unit" or "polymer unit" refers to a monomer or polymer portion of a copolymer molecule or blend component that includes a different molecular structure, compared to another portion of the copolymer or blend.

These terms may be defined with additional language in the remaining portions of the specification.

DETAILED DESCRIPTION

Figure 1B:
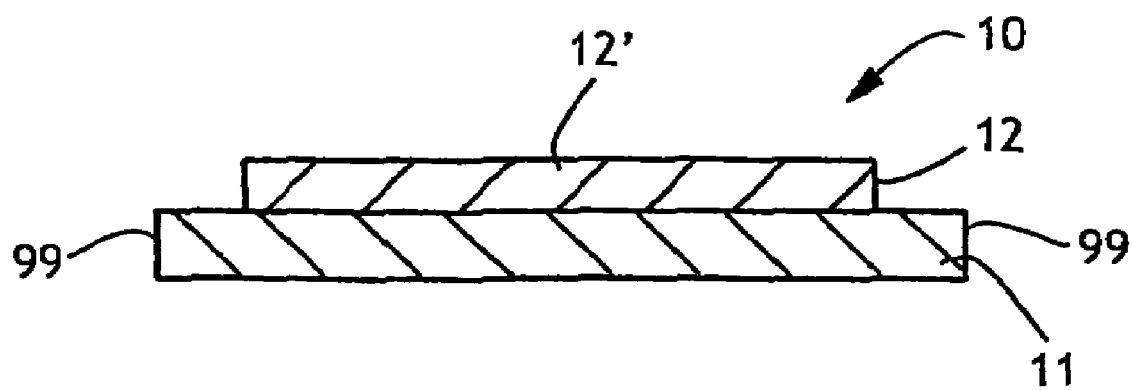
Figure 1C:
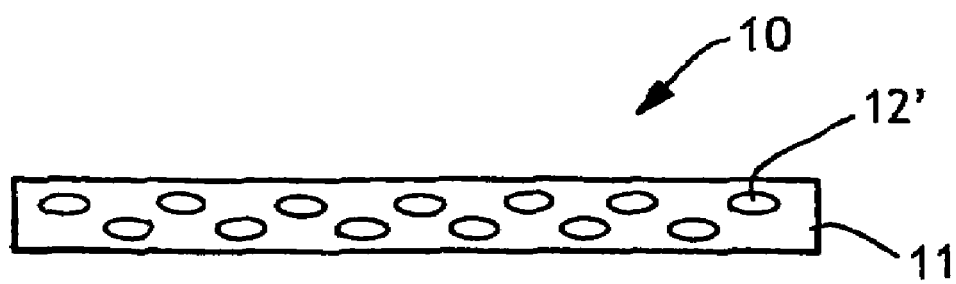
FIG. 1C is a cross-section of an absorbent composite of the present invention having a substrate layer impregnated with an absorbent material.

The absorbent composite of the present invention contains a substrate and an absorbent material applied to the substrate. The absorbent material may be a layer on the substrate, as is shown in FIGS. 1A and 1B, which are described in more detail below, or the absorbent material may be impregnated into the substrate, as is shown in FIG. 1C. With reference to FIG. 1A, which shows a cross-section of the absorbent composite of the present invention, the absorbent composite 10 has a substrate or support layer 11 and an absorbent layer 12. In one embodiment of the present invention, the absorbent layer may be formed on a surface of the substrate from an absorbent material 12'. As will be explained in more detail below, the absorbent material is prepared from a flexible superabsorbent binder polymer composition.

As is shown in FIG. 1A, the absorbent layer 12 may be coextensive with the substrate 11. However, in the present invention, it is not necessary that the absorbent layer 12 is coextensive with the substrate layer 11. That is, the absorbent layer 12 does not completely cover the substrate 11 to the outer edges 99 of the substrate. In an alternative embodiment of the present invention shown in FIG. 1B, the absorbent layer 12 containing the absorbent material 12' is not coextensive with the substrate 11, covering only a portion of the substrate 11 short of the outer edges 99 of the substrate 11. In another alternative embodiment of the present invention, the absorbent material may be placed within the substrate or impregnated into the substrate. This is shown in FIG. 1C, where the absorbent material 12' is placed within the substrate 11. In order for the absorbent material to be impregnated or otherwise placed within the substrate 11, the substrate should be prepared from a material which contains interstitial spaces that allow the absorbent material 12' to penetrate the surface of the substrate 11 and allow the absorbent material 12' to be within interstitial spaces within the substrate 11. Whether the absorbent is a layer on the substrate or placed within the substrate, the substrate acts as a support layer, supporting the absorbent material, and the absorbent layer is generally prepared on the substrate. It is noted that the absorbent material 12' may appear to be shown in FIG. 1C as a discrete phase or as discrete particles; however, the intent is to show that the flexible superabsorbent binder polymer composition 12' is impregnated into the substrate 11. Thus, the flexible superabsorbent binder polymer composition could be a continuous phase within the substrate.

In the present invention, the combined substrate and the flexible superabsorbent binder polymer composition have a light transmittance of at least 45%, as measured by the Light Transmittance Test (described below). In some aspects, the light transmittance of the absorbent composite of the present invention in an area containing the flexible superabsorbent binder polymer composition can be generally greater than 50%, such as at least 60%. For example, in some particular aspects, the light transmittance is in a range of 60% to 79%.

The substrate of the absorbent composite may comprise a wide variety of materials. In addition, the support layer can be liquid permeable or liquid impermeable. In some aspects, the support layer can be a film, a nonwoven web, a knitted fabric or a woven fabric, or a laminate of one or more of these materials. The only requirements for the substrate layer are that the support layer has a light transmittance of at least 45% as measured by the Light Transmittance Test, and that the support layer has sufficient integrity so that the flexible superabsorbent binder polymer composition may be placed on the substrate layer, or in the case of substrates with interstitial spaces, such as knitted fabrics, woven fabrics and nonwoven webs, or laminates containing these substrate materials, can be impregnated with the flexible superabsorbent binder polymer composition. In addition, the substrate should have sufficient flexibility so that the absorbent can be used in flexible absorbent articles. Particular examples of substrates include, but are not limited to, polyolefin films, spunbond nonwoven webs and laminates of polyolefin films and spunbond nonwoven webs, bonded-carded-webs, bonded-airlaid webs, coform, and woven fabrics such as cotton and wool cloth.

The light transmittance of the substrate can be affected in many different ways. For example, the addition of coloring agents, such as dyes, pigments, fillers and other similar materials in the raw materials used to make the substrate may reduce the light transmittance of the substrate formed from the raw materials. One way to improve the light transmittance of the substrate is to reduce, or even eliminate, the amount of coloring agents, pigments, fillers and other materials which may cause a reduction of light transmittance from the raw materials used to make the substrate. In one aspect, the substrate contains less than about 2% by weight fillers, pigments or coloring agents which can reduce the light transmittance of the substrate, such as less than about 1% by weight of fillers, pigments or coloring agents which can reduce the light transmittance of the substrate. In one particular aspect, the substrate is substantially free of coloring agents, pigments, fillers and other similar materials which may reduce the light transmittance of the substrate.

Additional methods for improving or sustaining the light transmittance of the substrate in the range described above is to limit the basis weight and thickness of the substrate to a minimum. However, care should be taken so that the substrate maintains sufficient strength. For example, when the substrate of the present invention is a film material, the film should have a thickness of less than about 1.0 mm (broad thickness), such as less than about 0.5 mm, and generally greater than about 0.01 mm. In particular aspects, the thickness of the film should be between about 0.02 mm and 0.25 mm.

In general, as the thickness of the film increases, the light transmittance of the film may be reduced. However, if the thickness of the film is less that about 0.01 mm, the substrate may be damaged during formation of the absorbent composite or during use of the absorbent composite, unless the film is reinforced in some manner, for example, by laminating it to a nonwoven web. For example, when the substrate is a nonwoven web, the basis weight should generally be below about 100 gsm;

however, the basis weight is only limited by the overall light transmission of the absorbent composite. Therefore, the nonwoven substrate could have a basis weight in excess of 100 gsm. In some aspects, the basis weight of the nonwoven web should be between about 7 gsm and about 60 gsm, such as between about 10 gsm and about 40 gsm. In general, if the basis weight is above 100 gsm, the nonwoven web will tend to have a lower light transmittance, and if the basis weight is below about 7 gsm, the nonwoven web will tend to have insufficient strength to support the absorbent material.

In some aspects of the present invention, the flexible superabsorbent binder polymer composition may be placed directly on the substrate and can be directly joined or directly connected to the substrate, without the addition of adhesives, thereby forming a layer on the substrate. In other aspects, the flexible superabsorbent binder polymer composition can penetrate the substrate such that it will be impregnated into the support substrate. The flexible superabsorbent binder polymer composition may be applied to the substrate using any suitable application process, including slot coating, screen coating, knife over roll coating, or roll coating, either in a continuous coverage or a patterned coverage. Printing applications are other suitable application techniques, including gravure printing, screen, roll, rotary roll and jet printing. The flexible superabsorbent binder polymer composition may also be applied to the substrate using a spray application. The actual method of application of the flexible superabsorbent binder polymer composition to the substrate is not critical to the present invention. Once placed on the substrate, the flexible superabsorbent binder polymer composition is crosslinked, forming an absorbent coating on the substrate or forming a crosslinked absorbent material impregnated within the substrate.

In some aspects, the flexible superabsorbent binder polymer composition is the reaction product of a monomer solution including at least 15% by mass monoethylenically unsaturated carboxylic, sulphonic or phosphoric acid or salts thereof; an acrylate or methacrylate ester that contains an alkoxysilane functionality which can, upon exposure to water, form a silanol functional group which condenses to form a crosslinked polymer, a copolymerizable hydrophilic glycol containing an ester monomer; an initiator system; and a neutralizing agent.

In some aspects, the polymer composition can optionally include a plasticizer, a chain transfer agent, and/or a transition metal salt. Accordingly, in another aspect, the flexible superabsorbent binder polymer composition is the reaction product of a monomer solution including at least 15% by mass monoethylenically unsaturated carboxylic, sulphonic or phosphoric acid or salts thereof; a plasticizer; an acrylate or methacrylate ester that contains an alkoxysilane functionality, an initiator system; and a neutralizing agent.

In yet another aspect, the flexible superabsorbent binder polymer composition is the reaction product of a monomer solution including at least 15% by mass monoethylenically unsaturated carboxylic, sulphonic or phosphoric acid or salts thereof; a plasticizer; an acrylate or methacrylate ester that contains an alkoxysilane functionality, a chain transfer agent; a transition metal salt; an initiator system; and a neutralizing agent.

Suitable monomers that may be included to make a suitable superabsorbent polymer solution include carboxyl group-containing monomers, for example monoethylenically unsaturated mono or poly-carboxylic acids, such as (meth)acrylic acid (meaning acrylic acid or methacrylic acid; similar notations are used hereinafter), maleic acid, fumaric acid, crotonic acid, sorbic acid, itaconic acid, and cinnamic acid; carboxylic acid anhydride group-containing monomers, for example monoethylenically unsaturated polycarboxylic acid anhydrides (such as maleic anhydride); carboxylic acid salt-containing monomers, for example water-soluble salts (alkali metal salts, ammonium salts, amine salts, and the like) of monoethylenically unsaturated mono- or poly-carboxylic acids (such as sodium (meth)acrylate, trimethylamine (meth)acrylate, triethanolamine (meth)acrylate), sodium maleate, methylamine maleate; sulfonic acid group-containing monomers, for example aliphatic or aromatic vinyl sulfonic acids (such as vinylsulfonic acid, allyl sulfonic acid, vinyltoluenesulfonic acid, styrene sulfonic acid), (meth)acrylic sulfonic acids [such as sulfopropyl (meth)acrylate, 2 hydroxy-3-(meth)acryloxy propyl sulfonic acid]; sulfonic acid salt group-containing monomers, for example alkali metal salts, ammonium salts, amine salts of sulfonic acid group containing monomers as mentioned above; and/or amide group-containing monomers, for example vinylformamide, (meth)acrylamide, N-alkyl (meth)acrylamides (such as N-methylacrylamide, N-hexylacrylamide), N,N-dialkyl (meth)acryl amides (such as N,N-dimethylacrylamide, N,N-di-n-propylacrylamide), N hydroxyalkyl (meth)acrylamides [such as N-methylol (meth)acrylamide, N-hydroxyethyl (meth)acrylamide], N,N-dihydroxyalkyl (meth)acrylamides [such as N,N dihydroxyethyl (meth)acrylamide], vinyl lactams (such as N-vinylpyrrolidone).

Suitably, the amount of monoethylenically unsaturated carboxylic, sulphonic or phosphoric acid or salts thereof relative to the weight of the flexible superabsorbent binder polymer composition may range from about 15% to about 99.9% by weight. In some aspects, the levels of monoethylenically unsaturated carboxylic, sulphonic or phosphoric acid, or salts thereof, may be between about 20% and about 99.9% by weight of the flexible superabsorbent binder polymer composition, such as between about 25% and about 90% by weight of the flexible superabsorbent binder polymer composition, or between about 30% and about 80% by weight of the flexible superabsorbent binder polymer composition, or between about 50% and about 70% by weight of the flexible superabsorbent binder polymer composition for some intended uses.

The acid groups are desirably neutralized to the extent of at least about 25 mol %, that is, the acid groups are preferably present as sodium, potassium or ammonium salts. In some aspects, the degree of neutralization is preferably at least about 50 mol %.

Organic monomers capable of co-polymerization with monoethylenically unsaturated carboxylic, sulphonic or phosphoric acid or salts thereof, which monomers contain a trialkoxysilane functional group or a moiety that reacts with water to form a silanol group, are useful in the practice of this invention. The trialkoxysilane functional group has the following structure

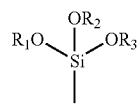

wherein R1, R2 and R3 are alkyl groups independently having from 1 to 6 carbon atoms.

The term "monomer(s)" as used herein includes monomers, oligomers, polymers, mixtures of monomers, and any other reactive chemical species which is capable of co-polymerization with monoethylenically unsaturated carboxylic, sulphonic or phosphoric acid or salts thereof. Ethylenically unsaturated monomers containing a trialkoxysilane functional group are appropriate for this invention and may be desired. Desired ethylenically unsaturated monomers include acrylates and methacrylates, such as acrylate or methacrylate esters that contain an alkoxysilane functionality. A particularly desirable ethylenically unsaturated monomer containing a trialkoxysilane functional group is methacryloxypropyl trimethoxy silane, commercially available from Dow Corning (having a place of business in Midland, Mich., U.S.A.) under the trade designation Z-6030 SILANE and from Degussa (having a place of business in Parsippany, N.J., U.S.A) under the trade name DYNASYLAN MEMO. Other suitable ethylenically unsaturated monomers containing a trialkoxysilane functional group include, but are not limited to, methacryloxyethyl trimethoxy silane, methacryloxypropyl triethoxy silane, methacryloxypropyl tripropoxy silane, acryloxypropylmethyl dimethoxy silane, 3 acryloxypropyl trimethoxy silane, 3 methacryloxypropylmethyl diethoxy silane, 3 methacryloxypropylmethyl dimethoxy silane, and 3 methacryloxypropyl tris(methoxyethoxy)silane. However, it is contemplated that a wide range of vinyl and acrylic monomers having trialkoxysilane functional groups or a moiety that reacts easily with water to form a silanol group, such as a chlorosilane or an acetoxysilane, provide the desired effects and are effective monomers for copolymerization in accordance with the present invention.

Whereas most superabsorbent polymers require the addition of an internal crosslinker to reinforce the polymer, the flexible superabsorbent binder polymer composition of the present invention does not require the addition of a crosslinking agent because the organic monomers including the trialkoxysilane functional act as a latent internal crosslinker. The internal crosslinker allows the superabsorbent binder polymer composition to be formed by coating the water-soluble precursor polymer onto the substrate and then removing the water to activate the latent crosslinker.

In addition to monomers capable of co-polymerization that contain a trialkoxysilane functional group, a monomer capable of co-polymerization that can subsequently be reacted with a compound containing a trialkoxysilane functional group or a moiety that reacts with water to form a silanol group can also be used. Such a monomer may contain, but is not limited to, an amine or an alcohol. An amine group incorporated into the co-polymer may subsequently be reacted with, for example, but not limited to, (3-chloropropyl) trimethoxysilane. An alcohol group incorporated into the co-polymer may subsequently be reacted with, for example, but not limited to, tetramethoxysilane.

The amount of organic monomer having trialkoxysilane functional groups or silanol-forming functional groups relative to the weight of the polymeric binder composition may range from about 0.1% to about 15% by weight. Suitably, the amount of monomer should exceed 0.1% by weight in order to provide sufficient crosslinking upon exposure to moisture. In some aspects, the monomer addition levels are between about 0.1% and about 20% by weight of the flexible superabsorbent binder polymer composition, such as between about 0.5% and about 10% by weight of the flexible superabsorbent binder polymer composition, or between about 0.5% and about 5% by weight of the flexible superabsorbent binder polymer composition for some intended uses.

The flexible superabsorbent binder polymer composition can include a copolymerizable hydrophilic glycol containing an ester monomer, for example long chain, hydrophilic monoethylenically unsaturated esters, such as poly(ethylene glycol) methacrylate having from 1 to 13 ethylene glycol units. The hydrophilic monoethylenically unsaturated esters have the following structure:

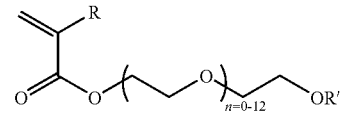

R' = H, alkyl, phenyl
R = H or CH$_3$

The amount of monoethylenically unsaturated hydrophilic esters relative to the weight of the polymeric binder composition thereof may range from 0 to about 75% by weight of monomer to the weight of the flexible superabsorbent binder polymer composition. In some aspects, the monomer addition levels are between about 10% and about 60% by weight of the flexible superabsorbent binder polymer composition; such as between about 20% and about 50% by weight of the flexible superabsorbent binder polymer composition, or between about 30% and about 40% by weight of the flexible superabsorbent binder polymer composition, for some intended uses.

In some aspects, the flexible superabsorbent binder polymer composition may also include a plasticizer, such as a hydrophilic plasticizer. Suitable hydrophilic plasticizers include, but are not limited to, polyhydroxy organic compounds such as glycerin and low molecular weight polyolefinic glycols such as polyethylene glycol (PEG) of molecular weight ranges from about 200 to about 10,000.

The amount of plasticizer relative to the weight of the flexible superabsorbent binder polymer composition thereof may range from 0 to about 75% by weight of the plasticizer to the weight of the flexible superabsorbent binder polymer composition. In some aspects, the plasticizer addition levels are from about 10% to about 60% by weight of the flexible superabsorbent binder polymer composition, such as from about 10% to about 40% by weight of the flexible superabsorbent binder polymer composition, for some intended uses.

In some aspects, the flexible superabsorbent binder polymer composition of the present invention may be made from monomers that include at least 15% by weight monoethylenically unsaturated monomer selected from carboxylic acid, carboxylic acid salts, sulphonic acid, sulphonic acid salts, phosphoric acid, or phosphoric acid salts; an initiator system; and an acrylate or methacrylate ester that contains a group readily transformed into a silanol functionality by subsequent reaction with water, wherein the resulting flexible superabsorbent binder polymer composition has an average molecular weight of from about 100,000 to about 650,000 g/mole, such as about 100,000 to about 300,000 g/mole, and the superabsorbent polymer composition has a viscosity of less than about 10,000 cps and a residual monoethylenically unsaturated monomer content of less than about 1000 ppm.

The superabsorbent polymer composition may be prepared by adding a solution of the above monomers to an initiator system, at a suitable temperature, to generate free radicals, for example between about 50° C. and about 90° C. An initiator system may be prepared by dissolving an initiator in a solvent. Initiators are used to start the polymerization of a monomer. The action of an initiator is similar to that of a catalyst, except that the initiator is generally consumed in the reaction. Possible solvents include, but are not limited to water, and alcohols such as ethanol. A variety of initiators may be useful in the practice of this invention. The polymerization initiator system may be activated using a variety of methods including, but not limited to, thermal energy, radiation, redox chemical reactions, thermal initiators and other methods known in the art. One suitable class of initiators is organic peroxides and azo compounds, with benzoyl peroxide and azobisisobutyronitrile (AIBN), as examples. Examples of suitable initiators include t-amylperoxypivalate, 2,2'-Azobis(2,4'-dimethylvaleronitrile) (V65B), sodium persulfate (NAPS); and 2,2'-azobis-2-amidinopropanedihydrchloride (ABAH). Suitable amounts of initiators depend upon the particular initiator. Examples include, but are not limited to, at least about 0.003 mol/mol of t-amylperoxypivalate; at least about 0.01 mol/mol of 2,2'-Azobis(2,4'-dimethylvaleronitrile); at least about 200 ppm of sodium persulfate; and at least about 200ppm of 2,2'-azobis-2-amidinopropanedihydrchloride.

Compounds containing an O—O, S—S, or N=N bond may be used as thermal initiators. Compounds containing O—O bonds, such as peroxides, are commonly used as initiators for polymerization. Examples of peroxide initiators include alkyl, dialkyl, diaryl and arylalkyl peroxides such as cumyl peroxide, t-butyl peroxide, di-t-butyl peroxide, dicumyl peroxide, cumyl butyl peroxide, 1,1-di-t-butyl peroxy-3,5,5 trimethylcyclohexane, 2,5-dimethyl-2,5-di(t-butylperoxy)hexane, 2,5-dimethyl-2,5 bis(t-butylperoxy)hexyne-3 and bis(a-t-butyl peroxyisopropylbenzene); acyl peroxides such as acetyl peroxides and benzoyl peroxides; hydroperoxides such as cumyl hydroperoxide, t-butyl hydroperoxide, p-methane hydroperoxide, pinane hydroperoxide and cumene hydroperoxide; peresters or peroxyesters such as t-butyl peroxypivalate, t amylperoxypivalate, t-butyl peroctoate, t-butyl perbenzoate, 2,5-dimethylhexyl-2,5 di(perbenzoate) and t-butyl di(perphthalate); alkylsulfonyl peroxides; dialkyl peroxymonocarbonates; dialkyl peroxydicarbonates; sodium persulfate, 2,2'-Azobis(2,4'-dimethylvaleronitrile), 2,2'-azobis-2-amidinopropanedihydrchloride diperoxyketals; and ketone peroxides such as cyclohexanone peroxide and methyl ethyl ketone peroxide. In one particular aspect of the present invention, an organic initiator, t-amylperoxypivalate (TAPP) that decomposes very fast to form a stable ethyl ($CH_3CH_2$.) free radical was utilized to reduce the residual monoethylenically unsaturated monomer significantly.

A redox initiator system where free radicals are generated by oxidation-reduction reactions without the application of heat can be used for the polymerization of the monomer solution to make the flexible superabsorbent binder polymer composition. In this method, polymerization is started by adding either one of oxidizing or reducing components of the initiator system to the rest of the solution mixture of monomers and other components of the redox initiator system. Suitable oxidizing components of the redox initiator system include, but are not limited to, hydrogen peroxide, alkali metal persulfates, ammonium persulfate, alkalihydroperoxides, peresters, diacryl peroxides, silver salts and combinations thereof. Suitable reducing components of the initiator system include, but are not limited to, ascorbic acid, alkali metal sulfites, alkali metal bisulfites, ammonium sulfite, ammonium bisufite, alkali metal hydrogen sulfites, ferrous metal salts such as ferrous sulfates, sugars, aldehydes, primary and secondary alcohols, and combinations thereof. A combination of redox and thermal initiators can also be used. A redox initiator system that comprises hydrogen peroxide, ferrous sulfate and ascorbic acid coupled with thermal initiator sodium persulfate (NAPS) was found to reduce the residual monoethylenically unsaturated monomer significantly in aqueous polymerization of the present invention while yielding a weight average molecular weight of superabsorbent polymer in the target range of about 100,000 to about 650,000 g/mole, such as about 1000,000 to about 300,000 g/mole.

A chain transfer agent that can limit the polymer chain growth during the polymerization and thereby can control the molecular weight and viscosity of flexible superabsorbent binder polymer solution can additionally be used in the polymerization solution. Suitable chain transfer agents include, but are not limited to, alcohols such as isopropyl alcohol, organic acids such as formic acid, inorganic acids such as hypophosphorus acid, organic amines such as triethylamine and combinations thereof. In one aspect, hypophosphorus acid was found to be an effective chain transfer agent for the flexible superabsorbent binder polymer composition.

The amount of chain transfer agent relative to the weight of monoethylenically unsaturated carboxylic, sulphonic or phosphoric acid or salts monomers may range from 0.1 to about 20% by weight of the chain transfer agent to the weight of the monomers. In some aspects, the chain transfer agent addition levels can be between bout 5% and about 15% by weight of the monomer, such as between about 2% and bout 10% by weight of the monomer, or between about 0.5% and about 1% by eight of the monomer to obtain desired molecular weight and viscosity levels of the lexible superabsorbent binder polymer composition, for some intended uses.

The method to make the flexible superabsorbent polymer composition of the resent invention may further include a transition metal salt. Examples of some uitable transition metals for the transition metal salt include, but are not limited to, candium, titanium, vanadium, chromium, manganese, iron, cobalt, nickel, copper, inc, silver, and the like. For instance, a transition metal salt may be combined with the flexible superabsorbent binder polymer compositions before, during, and/or after its formation. For instance, some transition metal salts that may be used in the present invention include, but are not limited to, halides, such as iron chloride, copper chloride, sulfates, nitrates, acetates, oxalates, carbonates, and so forth. Iron sulfate may be used in the present invention.

In some aspects of the present invention, a new source of crosslinking having silanol functionality may be added to the superabsorbent binder polymer composition just before the concentrated solution is applied to a substrate. The added source of silanol crosslinking functionality may, in effect, activate the solution for gellation as it is being applied to the substrate. Potential sources of silanol (Si—OH) functionality include, but are not limited to silica nano particles, such as SNOWTEX ST-40 (available from Nissan Chemical—America Corporation, having a place of business located in Houston, Tex., U.S.A.); silica aerogel particles, such as SYLOID silica (available from Grace Davison, a division of W.R. Grace & Co., having a place of business in Columbia. Md., U.S.A.); clays with Si—OH surface, such as Kaolin, bentonite, or attapolgite; and zeolites. In addition, soluble sources of silanol can be added, such as silicates, or in the form of monomeric silanes that are readily hydrolyzed to silanols, such as, but not limited to alkoxysilanes, for example, tetraethoxy silane (TEOS).

The source of silanol can be added in any suitable manner to provide sufficient mixing with the flexible superabsorbent binder polymer composition solution prior to coating onto the substrate. For example, two separate, metered, feed streams of the flexible superabsorbent binder polymer solution and silanol source may be combined at a Y-juncture with a downstream static mixer in the flow line to provide mixing.

Suitable ranges may be any that provide for a stable solution at a polymer concentration greater than 25%. Alkoxysilane functionality is incorporated into a base flexible superabsorbent binder polymer solution at an acrylate to silane mole ratio of 170:1. Flexible superabsorbent binder polymer composition with 75%, 50% and 25% of a base flexible superabsorbent binder polymer solution incorporation have been prepared. (Mole ratios of acrylate to silane in these polymers are 227:1, 340:1, and 680:1). Table 1 below shows the absorbent capacity data, based on the Centrifuge Retention Capacity Test (described below):

TABLE 1

| Polymer composition | CRC g/g |
|---|---|
| Standard composition: acrylate:Si—OH ratio 56:1 | 14.2 |
| 50% reduced alkoxysilane: acrylate to Si—OH ratio 112:1 | 21.4 |
| 50% reduced alkoxysilane: with kaolin added to reduce acrylate to Si—OH ratio to 20:1 | 15.1 |
| 50% reduced alkoxysilane: with syloid silica added to reduce acrylate to Si—OH ratio to 20:1 | 14.6 |
| 50% reduced alkoxysilane: with tetraethoxy silane added to reduce acrylate to Si—OH ratio to 20:1 | 17.1 |

As demonstrated in Table 1, reducing the alkoxysilane incorporation increased the Centrifuge Retention Capacity (CRC) due to lower crosslink density, compared to a base flexible superabsorbent binder polymer composition. Addition of sources of silanol, even to levels greater than a base flexible superabsorbent binder polymer composition, provides a higher CRC than a base flexible superabsorbent binder polymer composition, even with higher crosslinking potential. Once the flexible superabsorbent binder polymer composition is applied to the substrate, crosslinking can be moisture-induced by hydrolysis and condensation of alkoxysilanes. Activation by this method can take place during solvent removal or after solvent removal by exposure to air at ambient humidity. Solvent may be removed from the substrate either by evaporating the solvent or by any other suitable technique. Heat or radiation may be applied to increase the rate of the process. Recovery of the solvent is a part of the process and methods for this are widely known to those skilled in the art.

In addition, modifying agents such as compatible polymers, plasticizers, colorants, and preservatives may be incorporated in the flexible superabsorbent binder polymer composition of the present invention, provided that the resulting support layer has a light transmittance of at least 45% as measured by the Light Transmittance Test.

In some aspects of the present invention, the flexible superabsorbent binder polymer composition of the present invention may be prepared in an aqueous solution by the process including the steps of: a) preparing an initiator system solution; b) preparing a monomer solution including monoethylenically unsaturated monomers, one of which includes an alkyloxysilane functionality; c) mixing the initiator system and the monomer solution to form a polymerization solution; d) heating the polymerization solution to promote a reaction of the polymerization solution; e) cooling the polymerization solution; and f) neutralizing the polymer of step e) to at least about 25 mole % to form a flexible superabsorbent binder polymer composition, the dry polymer of which a residual monoethylenically unsaturated monomer content has less than about 1000 ppm. In addition, the polymer composition may have a weight average molecular weight of from about 100,000 to about 650,000 g/mole, such as from about 100,000 to about 300,000 g/mole, and/or a viscosity after 16 hours of less than about 10,000 cps. Furthermore, the flexible superabsorbent binder polymer composition may have a solids content of at least about 24% by weight.

In other aspects of the present invention, the flexible superabsorbent binder polymer composition of the present invention may be prepared in an aqueous solution by the process including the steps of: a) preparing a monomer solution including an initiator system that includes one component of a redox initiator; a chain transfer agent; a plasticizer; a cross-linker monomer that contains an alkoxysilane functionality; and monoethylenically unsaturated monomers, one of which includes a functionality wherein the acid groups are neutralized to at least 25 mole %; b) adding another component of the redox initiator to the monomer solution mixture of step a) to polymerize the monomer solution mixture of a); c) cooling the polymerization solution to a temperature less than 30° C.; d) adding a similar solution mixture of step a) to the polymerization solution of step c); e) adding a transition metal salt to the solution of step d); f) polymerizing the solution of step e); and g) optionally neutralizing the polymer of step f) to form a flexible superabsorbent binder polymer composition having a average molecular weight of from about 100,000 to about 650,000 g/mole, such as from about 100,000 to about 300,000 g/mole, and/or the superabsorbent polymer composition having a viscosity after 16 hours of less than about 10,000 cps and/or a residual monoethylenically unsaturated monomer content of less than about 1000 ppm. Furthermore, the flexible superabsorbent binder polymer composition may have a solids content of at least about 24% by weight.

In still other aspects of the present invention, the flexible superabsorbent binder polymer composition of the present invention may be prepared in an aqueous solution by the process including the steps of: a) preparing a monomer solution including an initiator system, a chain transfer agent, an initiating system, a plasticizer, a cross-linker monomer that contains an alkoxysilane functionality, monoethylenically unsaturated monomers, one of which includes a functionality wherein the acid groups are neutralized to at least 25 mole %; b) polymerizing the monomer solution mixture of step a) to promote a polymerization reaction; c) cooling the polymerization solution to a temperature of less than about 30° C.; d) adding a second monomer solution, neutralizing agent and plasticizer to the polymerization solution of step c); e) adding a transition metal salt to the solution of step d); f) further reacting the solution of step e); and g) optionally, further neutralizing the polymer of step f) to form a flexible superabsorbent binder polymer composition having a weight average molecular weight of from about 100,000 to about 650,000 g/mole, such as about 100,000 to about 300,000 g/mole, and/or a viscosity after 16 hours of less than about 10,000 cps and/or a residual monoethylenically unsaturated monomer content of less than about 1000 ppm. Furthermore, the flexible superabsorbent binder polymer composition may have a solids content of at least about 24% by weight.

When placed on a substrate and crosslinked, the flexible superabsorbent binder polymer composition forms an absorbent layer on the substrate, or may be impregnated into the substrate. Accordingly, as described above, the flexible superabsorbent binder polymer composition forms a superabsorbent layer on the substrate or a superabsorbent within the substrate. It is desirable that the absorbent layer has a high level of light transmittance. The level of light transmittance of the absorbent material is not critical to the present invention provided that the absorbent composite containing the substrate and the absorbent layer has a light transmittance of at least 45%, as measured by the Light Transmission Test. However, in general, it is desirable that the absorbent material have a light transmittance as high as possible. Methods for controlling the light transmittance of the absorbent layer include, but are not limited to, reducing or eliminating the amounts of coloring agents, pigments, fillers and the like which may cause a reduction of light transmittance. In some aspects of the present invention, the absorbent binder composition can contain less than about 2% by weight fillers, pigments and/or coloring agents which can reduce the light transmittance of the resulting absorbent layer, such as less than about 0.5% by weight of fillers, pigments and/or coloring agents which can reduce the light transmittance of the resulting absorbent material of the composite. In other aspects, it is desirable that the flexible superabsorbent binder polymer composition is substantially free of coloring agents, pigments, fillers and other similar materials which may reduce the light transmittance of the resulting absorbent layer.

Other methods for improving or maintaining light transmittance of the absorbent composite in the desired range described above include keeping the basis weight and/or thickness of the absorbent material in the composite of any resulting absorbent layer to a minimum, while providing sufficient absorbency to the absorbent articles. For example, while keeping the thickness and basis weight to a minimum, care should be taken so the absorbent composite has sufficient absorbing capacity. In some aspects, the absorbent material should have a basis weight of about 2 gsm to about 200 gsm on a solids basis and/or the layer should have a thickness less than 1.0 mm (broad thickness), such as between about 5 gsm and about 100 gsm on a solids basis and/or a thickness of less than about 0.5 mm, or between about 10 gsm and about 75 gsm on a solids basis and/or a thickness of less than about 0.3 mm (such as in the range of about 0.01 mm to about 0.3 mm).

In general, as the basis weight or thickness of the flexible superabsorbent binder polymer composition layer increases, the light transmittance of the absorbent composite may be reduced. However, if the basis weight or thickness of the flexible superabsorbent binder polymer composition layer is reduced, the capacity of the absorbent composite may also be reduced. It has been discovered that if the flexible superabsorbent binder polymer composition is applied in the ranges described above, the absorbent layer formed from the flexible superabsorbent binder polymer composition will have sufficient absorbency for most intended uses of the absorbent composite, while still providing a desired degree of translucence to the composite so that it will blend in with the use environment. In addition, the amount of the flexible superabsorbent binder polymer composition may be changed to meet a desired or needed absorbency for the absorbent article.

With reference to FIGS. 1A-1C, the substrate 11 may be a liquid permeable material or a liquid impermeable material. In some aspects, when the flexible superabsorbent binder polymer composition 12' is formed on a liquid permeable substrate, the absorbent composite 10 may need an additional liquid impermeable layer for the absorbent composite to fully contain and hold an insulting fluid. As a result, the absorbent composite of the present invention may contain at least one additional layer. The additional layer may be a liquid permeable material or a liquid impermeable material. Suitable additional layers include both liquid permeable materials or liquid impermeable materials. For example, the additional layer may include, but is not limited to, a film, a nonwoven web, a knitted fabric or a woven fabric, or a laminate of one or more of these materials. The only requirement for the additional layer is that it has a light transmittance of at least 45% as measured by the Light Transmittance Test.

In addition, the additional layer should have sufficient flexibility so that the absorbent composite can be used in an absorbent article that is flexible. Particular examples of substrates include, but are not limited to, polyolefin films, spunbond nonwoven webs and laminates of polyolefin films and spunbond nonwoven webs, bonded-carded-webs, bonded airlaid webs, coform, and woven fabrics such as cotton and wool cloths. There may be more than one additional layer present in the absorbent composite. Generally, it is desired that the one or more additional layers each have a light transmittance of at least 60%. As with the substrate layer, in some aspects of the present invention, the additional layer contains less than about 2% by weight fillers, pigments or coloring agents which can reduce the light transmittance of the additional layer, such as less than about 1% by weight fillers, pigments or coloring agents which can reduce the light transmittance of the additional layer. In one particular aspect, the additional layer is substantially free of coloring agents, pigments, fillers and other similar materials which may reduce the light transmittance of the additional layer.

Figure 2A:
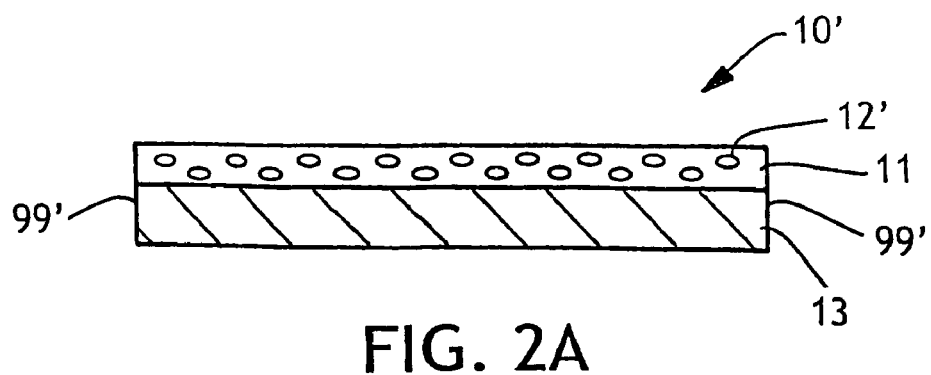
FIGS. 2A and 2B are each a cross-section of an absorbent composite of the present invention having a substrate layer impregnated with the absorbent material and an additional layer.
Figure 2B:
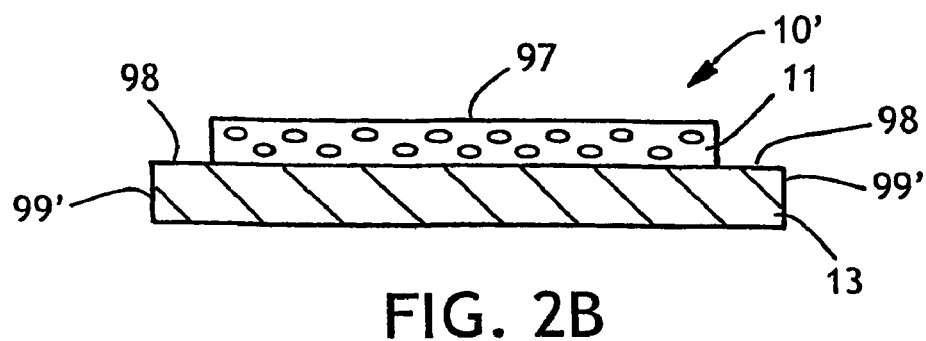

To obtain a better understanding of the absorbent composite with additional layers, attention is directed to FIGS. 2A and 2B. FIG. 2A shows an absorbent composite 10' having a substrate layer 11 impregnated with the flexible superabsorbent binder polymer composition 12' and an additional layer 13. The additional layer 13 is adjacent to the substrate 11 with the flexible superabsorbent binder polymer composition 12' impregnated therein. As is shown in FIG. 2A, the substrate 11 with the flexible superabsorbent binder polymer composition 12' impregnated therein is coextensive with the side edges 99' of the additional layer 13. In an alternative embodiment, shown in FIG. 2B, the substrate 11 having the flexible superabsorbent binder polymer composition 12' applied therein is positioned on the additional layer 13 such that the substrate and the flexible superabsorbent binder polymer composition therein is not coextensive with the edges 99 of the additional layer. As stated above in regard to FIG. 1C, it is noted that the flexible superabsorbent binder polymer composition 12' may appear to be shown in FIGS. 2A and 2B as a discrete phase or as discrete particles. However, the intent is to show that the flexible superabsorbent binder polymer composition 12' is impregnated within the substrate 11. That is, the flexible superabsorbent binder polymer composition 12' could be a continuous phase within the substrate 11.

Figure 2C:
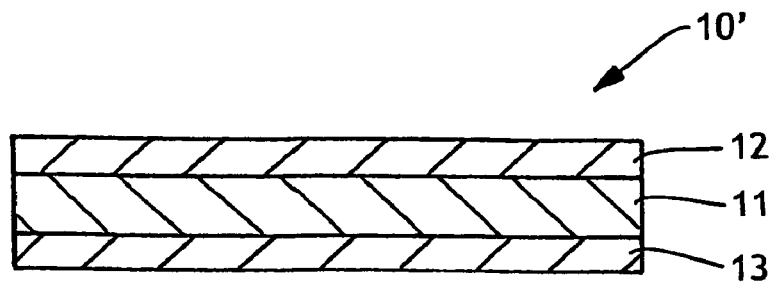
FIGS. 2C and 2D are each a cross-section of an absorbent composite of the present invention having a substrate layer, an absorbent layer and an additional layer.
Figure 2D:
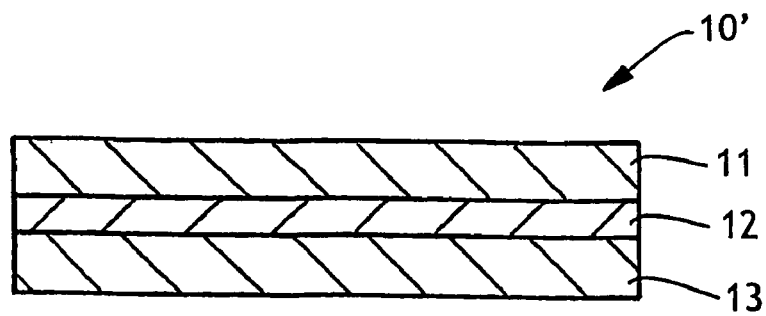

In addition, the substrate 11 may have the flexible superabsorbent binder polymer composition 12' applied as an additional layer on the substrate 11, as is shown in FIG. 2C. The additional layer 13 may be bonded to the substrate layer 11 using a known technique, such as adhesive bonding, pattern bonding using heat and pressure, ultrasonic bonding, stitching and other similar joining techniques. The layers of the absorbent composite may be held together using suitable bonding techniques, including those described above. In another aspect, the absorbent material 12 from the flexible superabsorbent binder polymer composition may adhesively hold the additional layer 13 to the substrate 11 as is shown in FIG. 2D. When a three layer structure absorbent composite is desired or prepared, the flexible superabsorbent binder polymer composition may be applied to one of layers 11 or 13 or both layers 11 and 13. The layers are brought together so that the flexible superabsorbent binder polymer composition contacts each layer of the substrate 11 and additional layer 13 of the absorbent composite. As a result, the flexible superabsorbent binder polymer composition and the resulting absorbent layer 12 are directly joined to the adjacent substrate 11 and additional layer 13, without an additional adhesive. This may be accomplished by applying the flexible superabsorbent binder polymer composition to facing surfaces of one or both layers 11 and 13, bringing the layers 11 and 13 together so that the flexible superabsorbent binder polymer composition contacts both layers, and crosslinking the flexible superabsorbent binder polymer composition to form the absorbent layer 12. In some aspects, crosslinking can be moisture-induced by hydrolysis and condensation of alkoxysilanes. For example, crosslinking of the flexible superabsorbent binder polymer composition can be induced by concentrating the composition through the removal of the water to promote condensation of silanols generated by hydrolysis of alkoxysilanes.

The flexible superabsorbent binder polymer composition layer may be formed on the substrate or support layer as a continuous layer having uniform thickness, or as a discontinuous or nonuniform layer which provides flow channels, liquid retention dams, or other desired attributes. However, because the absorbent layer 12 is intended as a sole or primary absorbent layer in the simplified absorbent article, the flexible superabsorbent binder polymer composition should be present in sufficient thickness and quantity, and over a sufficient area, to provide substantially all of the liquid absorption capacity that is required by the end use application. Alternatively, in some aspects, superabsorbent materials, such as superabsorbent particles, can be additionally incorporated into the absorbent binder to provide a portion of the liquid absorption capacity required by the end use application.

Because the flexible superabsorbent binder polymer composition is in contact with layers 11 and 13 as it is being formed, the resulting absorbent layer 12 adheres to the substrate layer and the additional layer 13 in addition to serving as an absorbent (fluid storage) layer. Thus, in some aspects of the present invention, the absorbent composite 10' can provide three layers bound together in sequence (i.e., a fluid receiving layer or backing layer, an absorbent layer, and a support layer) without intervening adhesive layers.

In other aspects, the flexible superabsorbent binder polymer composition may be prepared using a continuous process wherein the polymerization and/or neutralization reaction is carried out in a suitable reactor that conveys the resulting flexible superabsorbent binder polymer composition, upon completion of the polymerization reaction, directly to an apparatus for applying the composition onto the substrate layer 11 and/or the additional layer 13. Such a continuous process may be desirable where conditions, such as high heat, can cause premature crosslinking of the flexible superabsorbent binder polymer composition that would hinder application of the composition onto the substrate.

One advantage of the flexible superabsorbent binder polymer composition of the present invention is that it provides a water-soluble ionic polymer capable of sufficient spontaneous crosslinking within about 10 minutes, such as less than about 5 minutes, or less than about 1 minute, at a web temperature not more than about 150° C., to provide the flexible absorbent binder layer with an absorbent capacity of at least one (1) gram of fluid per gram of flexible superabsorbent binder polymer composition, such as at least three (3) grams of fluid per gram of flexible superabsorbent binder polymer composition, using the Centrifuge Retention Capacity Test (described below).

The crosslinking at web temperatures not more than about 150° C., such as not more than about 120° C., or not more than about 100° C., permits the flexible superabsorbent binder polymer composition to be applied to one or more substrate layers, and then crosslinked, without degrading or damaging the substrate. Significant crosslinking occurs within about 10 minutes, such as within about 8 minutes, or within about 6 minutes to provide an efficient, commercially feasible, cost-effective crosslinking process. The crosslinking may then continue until a flexible superabsorbent binder polymer composition having the desired absorbent capacity is obtained.

The ionic polymer may bear a positive charge, a negative charge, or a combination of both, and should have an ionic unit content of about 15 mole % or greater. The ionic polymer may include a variety of monomer units described above.

Figure 3A:
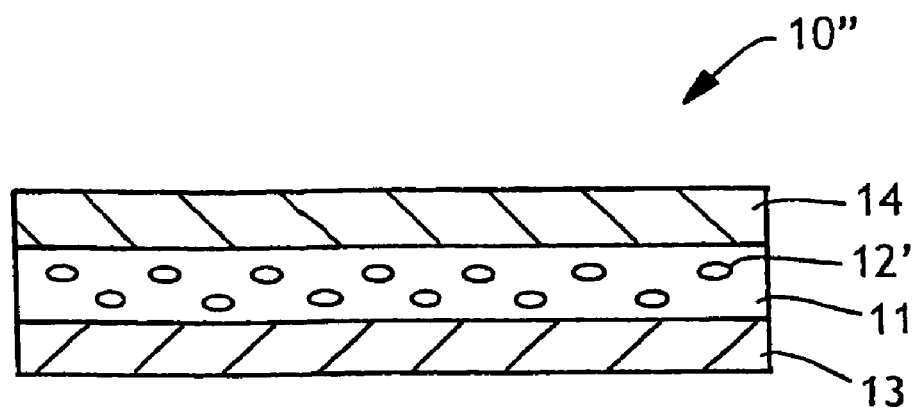
FIGS. 3A and 3B are each a cross-section of an absorbent composite of the present invention having a substrate layer impregnated with the absorbent material and two additional layers.

In other aspects of the present invention, the absorbent composite 10" may have a second additional layer 14. In this regard, attention is directed to FIG. 3A. The second additional layer 14 may be any of the same materials described above for the first additional layer 13. When the second additional layer is present, generally the substrate 11 and the flexible superabsorbent binder polymer composition 12' applied thereto are positioned between the first additional layer 13 and the second additional layer 14. Generally when two additional layers are present, one of the additional layers is a liquid impermeable material and the other additional layer is a liquid permeable material. As with the first additional layer, it is generally desirable that the second additional layer have a light transmittance of at least 60%, as measured by the Light Transmittance Test. In some aspects, the second additional layer contains less than about 2% by weight fillers, pigments or coloring agents which can reduce the light transmittance of the second additional layer, such as less than about 1% by weight fillers, pigments or coloring agents which can reduce the light transmittance of the second additional layer. In one particular aspect, the second additional layer is substantially free of coloring agents, pigments, fillers and other similar materials which may reduce the light transmittance of the second additional layer. In yet another particular aspect, the first and second additional layers each have a light transmittance of at least 80% and the overall absorbent composite has a light transmittance between about 55% and 79%, as measured by the Light Transmittance Test.

In other aspects of the present invention, the additional layer forms a backing layer of the composite 10". The backing layer serves to prevent any fluids absorbed by the substrate 11 and the flexible superabsorbent binder polymer composition 12' applied thereon from passing through the absorbent composite 10". Generally, the backing layer is fluid impermeable. In yet other aspects of the present invention, the second additional layer serves as a liner layer of the composite. The liner layer protects the substrate and the flexible superabsorbent binder polymer composition applied thereon during use of the absorbent composite 10". In addition, the liner may serve to protect the user of the absorbent composite 10" from having direct contact with any superabsorbent material that may optionally be present in the flexible superabsorbent binder polymer composition 12'.

In still other aspects of the present invention, the absorbent composite 10' may have two distinct areas of the composite which have different translucence, meaning different light transmittance. To obtain a better understanding of this aspect of the present invention, attention is again directed to FIG. 2B, which shows an absorbent composite 10' having a central region 97 and a perimeter region 98. The central region includes both the additional layer 13, which is typically a backing layer, in which the substrate 11 and the flexible superabsorbent binder polymer composition 12' applied thereon is adjacent the additional layer 13. The perimeter region 98 only includes the additional layer 13 or backing layer. In this aspect of the present invention, the perimeter region of the absorbent composite desirably has a light transmittance of at least 60% and the central region desirably has a light transmittance of at least 45%. In a particular aspect, the perimeter region of the absorbent composite has a light transmittance of at least 80% and the central region desirably has a light transmittance between about 55% and 79%. By having a difference in light transmission, a user of the absorbent composite can see the area of the composite which performs the majority of absorbency. In some aspects, this area is located in an insult target zone.

Figure 3B:
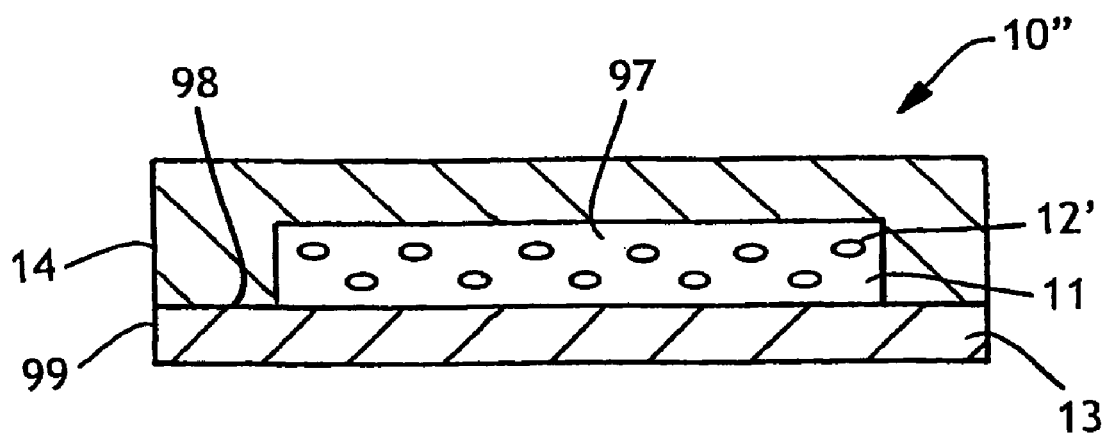

In yet another aspect of the present invention, as shown in FIG. 3B, when the second additional layer is present, the second additional layer 14 (e.g., a liner layer) and the first additional layer 13 (e.g., a backing layer) are present in the perimeter region 98 and the substrate 11 with the flexible superabsorbent binder polymer composition 12' applied thereto along with the first and second additional layers 13, 14 are present in the central region. The central region 97 and perimeter region 98 of the absorbent composite can have light transmission properties described above. As stated above, in regard to FIG. 1C, it is noted that the flexible superabsorbent binder polymer composition 12' may appear to be shown in FIGS. 3A and 3B as a discrete phase or discrete particles. However the intent is to show that the flexible superabsorbent binder polymer composition 12' is impregnated within the substrate 11. That is, the absorbent material can be a continuous phase within the substrate 11.

The absorbent composites of the present invention are relatively thin and can have a thickness in the range of about 0.05 mm to about 5 mm or more at a pressure of 1.35 kPa. Generally, it is desirable that the absorbent composites be as thin as possible while providing sufficient absorbency. In some aspects, the absorbent composites of the present invention have a thickness in the range of about 0.1 mm to about 2.0 mm, such as about 0.2 to about 1.2 mm. In addition, the absorbent composites of the present invention can have an absorbency greater than 0.8 g/g, such as up to about 10 g/g of the absorbent composite, or about 0.8 g/g to about 5 g/g of the absorbent composite, as measured by the Centrifuge Retention Capacity Test.

The translucent absorbent composite of the present invention also has the property of becoming soft and pliable under close-to-the-body conditions. The flexible superabsorbent binder polymer composition can be a very hydrophilic material with the ability to absorb water vapor. This property provides a benefit for thin absorbent articles because the relative stiffness of the article, when removed from the wrapper, allows the user to place the article in the undergarment with ease. However, when placed close to the body, the article becomes softer and more body conforming as a result of uptake of water vapor into the absorbent composite. This makes the absorbent composites of the present invention useable in absorbent articles, especially those absorbent articles used as sanitary napkins, pantiliners, diapers and the like.

The translucent absorbent composite of the present invention can be used on its own or as an absorbent component or absorbent layer in a wide variety of absorbent articles including, but not limited to, personal care absorbent articles, household/industrial absorbent articles and health/medical absorbent articles. In some aspects, the translucent absorbent composite of the present invention may be particularly suited for use in sanitary napkins, pantiliners, bandages, bed liners, furniture liners and pads as well as other absorbent articles that need both absorbency and transparency or translucence. Typically, absorbent articles have an absorbent layer, and a backing layer, which helps retain any absorbed fluids in the absorbent article. Most absorbent articles have a backing layer which is a liquid impermeable layer. The backing layer generally faces away from the fluid source, meaning that the absorbent layer is positioned between the fluid source and the backing layer. In some applications, such as a bandage, the backing layer may be apertured material, such as an apertured film, or material which is otherwise gas permeable, such as gas permeable films. In absorbent personal care articles such as pantiliners, the backing layer which is a liquid impermeable layer is often a garment facing layer. The backing layer is often referred to as a backsheet, baffle or outercover. Additional layers, such as a liner layer, also commonly referred to as a bodyside liner, may also be present in the absorbent article of the present invention.

In the present invention, the absorbent article is translucent, meaning that the absorbent article has a minimum light transmittance of about 45%. The absorbent layer of the absorbent article is prepared from an absorbent composite described above. In particular the absorbent layer is a substrate having the flexible superabsorbent binder polymer composition, described above, applied to the substrate. In an absorbent article prepared from the absorbent composite of the present invention, the absorbent layer of the absorbent article may contain the translucent absorbent composite as the main absorbent structure of the absorbent article. Layers of the absorbent composite of the present invention may also function as a layer of the absorbent article. For example, if the substrate layer 11 is a liquid impermeable material, the substrate layer of the absorbent composite could also function as the liquid impermeable layer of the absorbent article, for example, the backing layer of the absorbent article. To obtain a better understanding of an absorbent article of the present invention, attention is directed to FIG. 4. This figure illustrates an absorbent article 50 formed using an absorbent composite of the present invention. The absorbent article 50, as illustrated, includes three layers. These layers include a backing layer 52, also commonly referred to as a backsheet, baffle or outercover; an absorbent layer 56, which is formed from the absorbent composite of the present invention (e.g., a substrate with the flexible superabsorbent binder polymer composition applied thereto); and an optional bodyside liner layer 60, also commonly called a liquid intake layer. In some aspects of the present invention, it is desirable that the bodyside liner layer 60 is present in the absorbent article. Typically, the backing layer 52 of the absorbent article is a liquid impermeable layer made from a liquid impermeable material and the bodyside liner layer 60 is a liquid permeable layer and is prepared from a liquid permeable material.

In the present invention, the absorbent article contains the absorbent composite described above. In addition, the absorbent article of the present invention has a minimum light transmittance of at least 45% as measured by the Light Transmittance Test. In some aspects, the absorbent article has a minimum light transmittance of at least 50%, such as in the range of about 60% to about 79%.

In some aspects, the absorbent article 50 may include only two layers 52 and 56. In other aspects, the absorbent article 50 may include three layers 52, 56 and 60. Optionally, other layers may be included in the absorbent article on one or both sides of the absorbent layer. If additional layers are present in the absorbent article, the additional layers should not adversely affect the light transmission through the absorbent article (i.e., the minimum light transmittance should be at least 45%, as measured by the Light Transmittance Test). In any case, the absorbent article 50 of the present invention will have a simplified construction compared to conventional absorbent articles because: a) the flexible superabsorbent binder polymer composition-containing absorbent composite 56 (with or without superabsorbent particles) provides substantially all of the required absorbent capacity, and b) the absorbent layer 56 may bind to the adjacent layers 52 and 60 without intervening adhesive layers.

Referring again to FIG. 4, in some aspects of the present invention, the support layer 52 may be a liquid-impermeable outer cover material. Suitable outer cover materials include, without limitation, polyolefin films (e.g., films of polypropylene and polyethylene homopolymers and copolymers), breathable polyolefin films (e.g., stretch-thinned films formed from one or more polyolefins), and laminates of a breathable polyolefin film and a polyolefin nonwoven web (e.g., a spunbond web). In other aspects, the absorbent article 50 may be designed to include one or more functional layers, such as a dampness-inhibiting "spacer" structure, between the outer cover and the flexible superabsorbent binder polymer composition layer 56. In such instances, the support layer 52 may be any layer that is positioned directly below the absorbent layer 56 in the absorbent article 50. Depending on the application, the support layer 52 may be a nonwoven web, woven web, knitted fabric layer, cellulose layer, plastic film, plastic foam, staple fiber layer, stranded composite or another suitable material.

The bodyside liner 60 may be an apertured film, an open nonwoven layer such as a spunbond layer, bonded-carded-web or staple fiber web, an open-celled (e.g., reticulated) foam, a cellulose web, or any suitable open structure capable of receiving and/or distributing liquid. The fluid-receiving layer 60 may be homogeneous in the thickness direction or have a gradient structure. The desired composition of fluid receiving layer 60 may depend on whether the fluid-receiving layer 60 is used as a bodyside liner, or whether it is an interior fluid-receiving layer (e.g., a surge/transfer or compensation layer) used in addition to one or more other fluid receiving layers.

Figure 4:
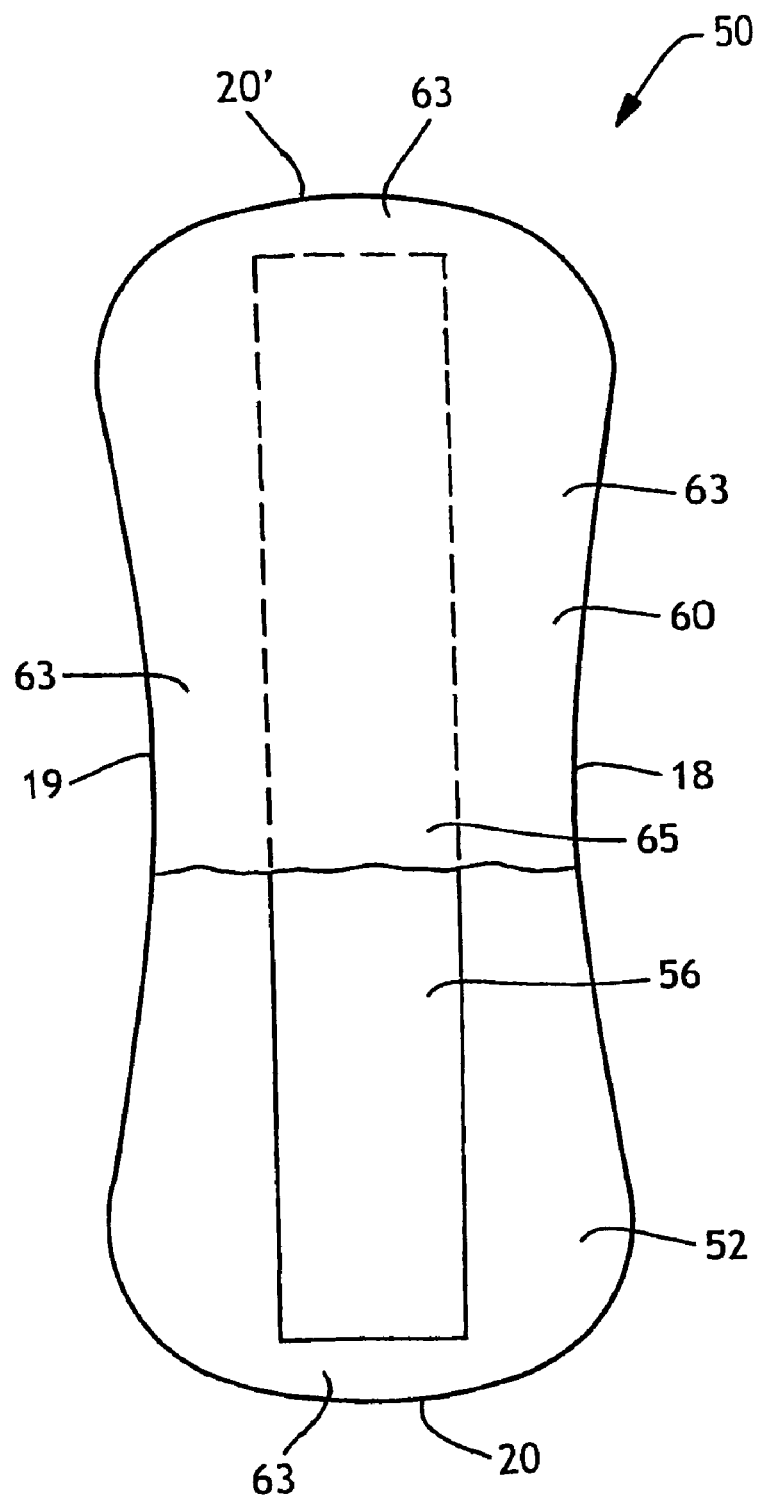
FIG. 4 is a top, cut-away view of an absorbent article of the present invention.

Other features may be present on the absorbent personal care article. The absorbent product 50 also has a first side 18 and a second side 19. The first and second sides 18,19, respectively, are the longitudinal sides of the elongated absorbent product. The sides can be contoured, for example, in a concave shape as shown in FIG. 4, or they can be linear. The sides can further include flaps (not shown) that extend laterally outward. Flaps are known in the art and are shown in, for example, U.S. Pat. No. 6,387,084 issued to VanGompel et al. or U.S. Pat. No. 4,589,876, issued to Van Tillburg, which are hereby incorporated by reference in a manner that is consistent herewith for its discussion of the flaps and flap attachment means and in its entirety. If these additional flaps are present, it is desirable that the flaps have a light transmittance of at least 60%, such as at least 80%, as measured by the Light Transmittance Test.

In another aspect of the present invention, the absorbent article 50 has a perimeter region 63 and a central region 65. The backing layer 52 and the bodyside liner 60, when present, are each present in both the perimeter region 63 and the central region 65. In a particular aspect, the absorbent layer 56 is only present in the central region 65 of the absorbent article 50. In other aspects, the perimeter region 63 may completely surround the central region 65, as is shown in FIG. 4, or the perimeter region 63 may be located on either side of the central region, such that the central region extends to the ends of the absorbent article. In this aspect of the present invention, the perimeter region may have a light transmittance of at least 60% and the central region may have a light transmittance of at least 45%, as measured by the Light Transmittance Test. In another aspect of this embodiment of the present invention, the perimeter region 63 of the absorbent article 50 can have a light transmittance of at least 80% and the central region 65 of the absorbent article 50 can have a light transmittance of between about 55% and about 79%. It is desirable that the light transmission in the absorbent area be different from the light transmission in the regions surrounding the absorbent, since the difference in light transmission allows the user to see the absorbent area, giving the user confidence that the liner will function as intended.

Figure 5:
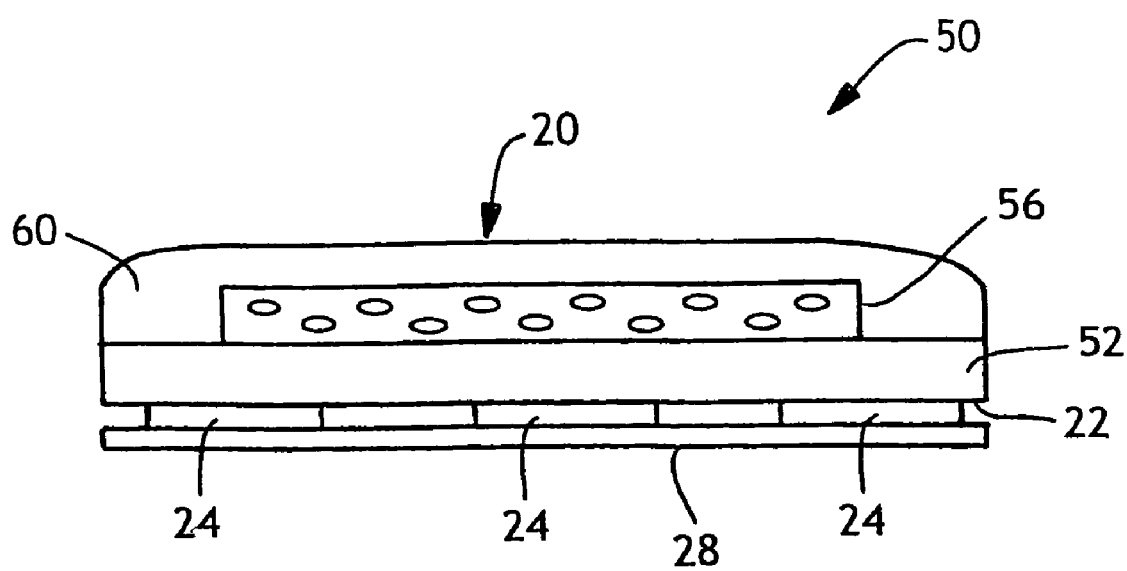
FIG. 5 is a cross-section of the absorbent article of the present invention.

Referring to FIG. 5, shown is a cross-section of an absorbent article 50 of the present invention. The absorbent article has a first body-side surface 20 and a second garment side surface 22. Applied to at least a portion of the second garment side surface 22 is a garment attachment adhesive 24. In various embodiments, the garment attachment adhesive 24 is configured as a single band of adhesive or as two or more spaced apart strips. Alternatively, the garment attachment adhesive 24 includes a swirl pattern of adhesive which encompasses a major portion of the second garment surface 22 of the absorbent article 50. As stated above in regard to FIG. 1C, it is noted that the flexible superabsorbent binder polymer composition appears to be shown in FIG. 5 as a discrete phase or as discrete particles. However the intent is to show that the absorbent material is impregnated into the substrate 11. That is, the absorbent material could be a continuous phase within the substrate 11.

A release strip 28, also known as a releasable peel strip, or simply a peel strip, may be removably secured to the garment attachment adhesive 24 and serves to prevent premature contamination of the adhesive 24 before the absorbent article 50 is secured to, for example, the crotch portion of an undergarment. In various embodiments, the garment attachment adhesive is designed to be secured to the inner crotch portion of an undergarment so as to keep the absorbent product in register with the body of the user. The release strip 28 may extend beyond one or both of the ends of the backing layer. In another aspect, the release strip may have a tab or other device to allow the user to see and grab the release strip so that the absorbent article 50 can be applied to an undergarment after the adhesive 24 is exposed.

In still other aspects of the present invention, the release strip 28 and the garment adhesive 24 also have a light transmission of at least 60%, as measured by the Light Transmittance Test. In this aspect, the strip may be prepared from a clear polymer film, which may have a pattern and/or words printed thereon so that the peel strip can be seen and removed by the user. In a particular aspect, the release strip 28 and the garment adhesive 24 each have a light transmission of at least 80%.

With the peel strip, garment adhesive, backing layer, absorbent layer and optionally the bodyside liner, the absorbent article should have a minimum light transmission of at least 45%, such as at least 60% or in the range of about 60% to about 79%.

Figure 6A:
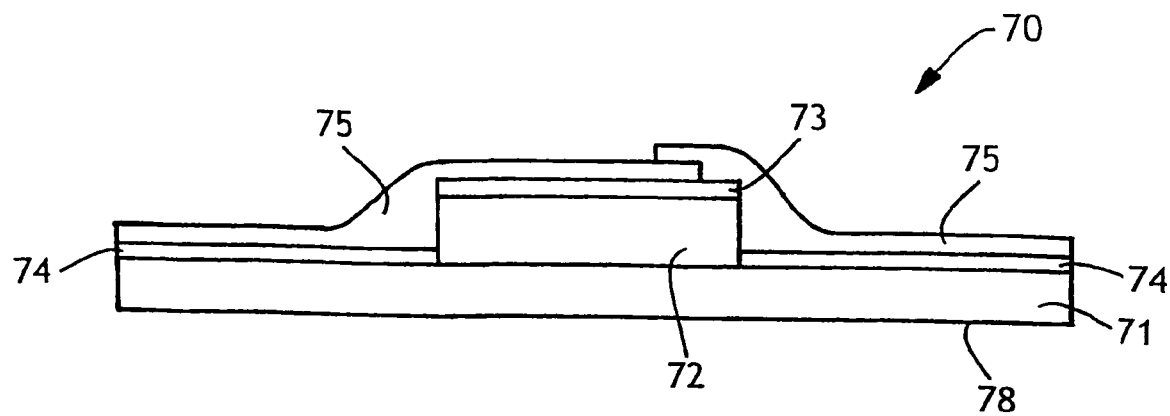
FIG. 6A is a cross-section side view of an absorbent bandage of the present invention.
Figure 6B:
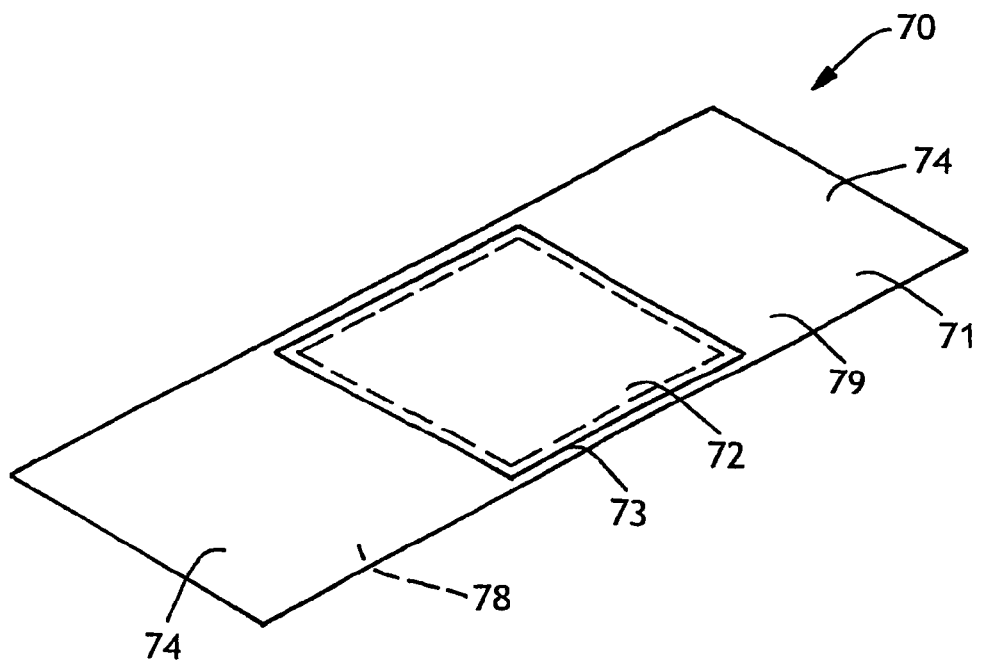
FIG. 6B is a top perspective view of an absorbent bandage of the present invention.

In addition to absorbent articles described above, the absorbent articles of the present invention may be used as an absorbent bandage. Attention is directed to FIGS. 6A and 6B, which show a possible configuration for a bandage of the present invention. FIG. 6A shows a cross-section view of the absorbent bandage with optional layers describe below. FIG. 6B shows a perspective view of the bandage of the present invention with some of the optional or removable layers not being shown. The absorbent bandage 70 has a strip 71 of material having a body-facing side 79 and a second side 78 which is opposite the body-facing side. The strip is essentially a backing layer and is desirably prepared from the same materials described above for the backing layer. In addition, the strip may be apertured material, such as an apertured film, or material which is otherwise gas permeable, such as a gas permeable film. The strip 71 supports an absorbent layer 72 which is attached to the body facing side 79 of the strip. In addition, an optional absorbent protective layer 73 may be applied to the absorbent layer 72 and can be coextensive with the strip 71. The absorbent layer 72 contains the absorbent composite of the present invention. In the present invention, the strip is desirably translucent, having a light transmission of at least 60%, as measured by the Light Transmittance Test. The absorbent bandage of the present invention has a minimum light transmission in the area of the absorbent layer 72 of at least 45%, as measured by the Light Transmittance Test.

The absorbent bandage 70 of the present invention may also have a pressure sensitive adhesive 74 applied to the body-facing side 79 of the strip 71. Any pressure sensitive adhesive may be used, provided that the pressure sensitive adhesive does not irritate the skin of the user. Suitably, the pressure sensitive adhesive is a conventional pressure sensitive adhesive which is currently used on similar conventional bandages. This pressure sensitive adhesive is preferably not placed on the absorbent layer 72 or on the absorbent protective layer 73 in the area of the absorbent layer 72. If the absorbent protective layer is coextensive with the strip 71, then the adhesive may be applied to areas of the absorbent protective layer 73 where the absorbent layer 72 is not located. By having the pressure sensitive adhesive on the strip 71, the bandage is allowed to be secured to the skin of a user in need of the bandage. To protect the pressure sensitive adhesive and the absorbent, a release strip 75 can be placed on the body facing side 79 of the bandage. The release liner may be similar to the release liner described above and may be placed on the body facing side of the bandage in a single piece (not shown) or in multiple pieces, as is shown in FIG. 6A.

In another aspect of the present invention, the absorbent layer of the bandage may be placed between a folded strip. If this method is used to form the bandage, the strip is suitably fluid permeable.

Figure 7:
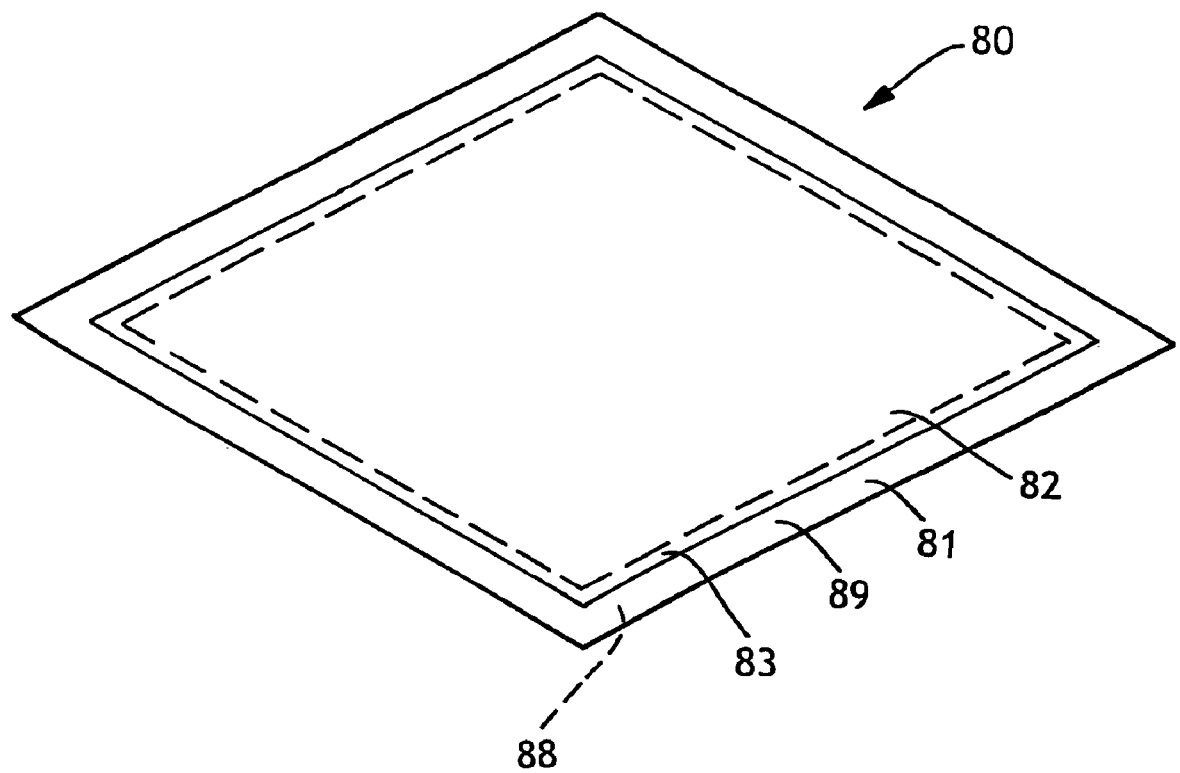
FIG. 7 is a top perspective view of an absorbent bed or furniture liner of the present invention.

Absorbent furniture and/or bed pads or liners are also included within the present invention. As is shown in FIG. 7, a furniture or bed pad or liner 80 (hereinafter referred to as a "pad") is shown in perspective. The pad 80 has a liquid impermeable backing layer 81 having a furniture-facing side or surface 88 and an upward facing side or surface 89 which is opposite the furniture-facing side or surface 88. The liquid impermeable backing layer 81 supports an absorbent layer 82 which is attached to the upward facing side 89 of the liquid impermeable backing layer. In addition, an optional absorbent protective layer 83 may be applied to the absorbent layer. The absorbent layer contains the absorbent composite of the present invention. The substrate layer of the absorbent composite can be the liquid impermeable layer 81 or the absorbent protective layer 83 of the pad. In the alternative, in aspects where the absorbent composite has three layers, the three layers of the absorbent composite can include the liquid impermeable layer 81, the absorbent layer 82 and the absorbent protective layer 83. In the present invention, the liquid impermeable layer is desirably translucent, having a light transmission of at least 60%, as measured by the Light Transmittance Test. The absorbent pad of the present invention has a light transmission of at least 45%, as measured in the area of the pad 80 having the absorbent layer 82. In some particular aspects, the absorbent pad 80 has a minimum light transmission of at least 60% in the area of the absorbent layer 82, such as about 55% to about 79%. As a result, the absorbent pad will blend in with the material of the furniture it is used on, providing the user with a discreet means to use the furniture pad without having others easily recognize that the user is in need of the absorbent furniture pad.

To hold the pad in place, the furniture-facing side 88 of the pad may contain a pressure sensitive adhesive, a high friction coating or other suitable material which will aid in keeping the pad in place during use. The pad of the present invention can be used in a wide variety of applications including placement on chairs, sofas, beds, car seats and the like to absorb any fluid which may come into contact with the pad.

In some aspects, the absorbent articles of the present invention may be prepared by placing the absorbent composite onto a backing layer and adding the optional liner layers. In other aspects, the absorbent articles may be cut from an absorbent composite sheet having the one or more additional layers described above.

In another aspect of the present invention, provided is an absorbent article comprising a body contacting surface, a surface opposed to the body contacting surface, an absorbent core positioned between the body contacting surface and the surface opposed to the body contacting surface, longitudinal edges extending along an edge of absorbent core and flaps. The flaps can extend from the longitudinal edges of the absorbent article and the flaps can contain an absorbent material that is capable of absorbing fluids. In some aspects, the flaps have a light transmittance of at least 45%, as measured by the Light Transmittance Test. In a particular aspect, the light transmittance of the flaps is at least 60%. The absorbent of the flaps is formed from the flexible superabsorbent binder polymer composition described above. In some aspects, a portion of the entire flap may contain the flexible superabsorbent binder polymer composition. In other aspects, the flaps of the absorbent articles may contain the absorbent composite of the present invention. In the absorbent article of this embodiment of the present invention with flaps, the absorbent layer may be an absorbent layer conventionally used in the art or may be the absorbent layer described above. In some aspects, the body contacting surface may be the bodyside liner described above, and the surface opposed the body-contacting surface may be the backsheet described above. Desirably, the flaps are prepared from a laminate of the body contacting surface and the surface opposed the body contacting surface.

It has been discovered that the absorbent composite of the present invention tends to become more flexible during use. As a result, the flexible articles containing the composite have a stiffness that convey to the user that they have the ability to absorb and retain fluids, but at the same time they become less stiff and more comfortable as the articles are being used or worn.

The present invention may be better understood with reference to the following test procedures and examples.

Test Procedures

Light Transmittance Test

Light transmittance (also referred to herein as light transmission) is measured consistent with ASTM D-1300 utilizing a GARDNER HAZE GUARD PLUS Model #4725 (available from BYK Gardner, having a place of business located in Columbia, Md., U.S.A.). In particular, a flat sample of the material to be tested is placed in the round holder having approximately a 60 mm diameter. Measurements are then taken by placing the flat sample in the measuring port. The haze port is used for measuring light transmittance. A series of five samples are measured and the average value of the five samples provides the light transmittance. Haze and clarity may also be measured using the GARDNER HAZE GUARD PLUS unit.

Centrifuge Retention Capacity (CRC) Test

As used herein, the Centrifuge Retention Capacity (CRC) is a measure of the Absorbent Capacity of the flexible superabsorbent binder polymer composition retained after being subjected to centrifugation under controlled conditions. The CRC can be measured by placing a sample of the material to be tested into a water-permeable bag that will contain the sample while allowing the test solution (0.9 percent NaCl solution) to be freely absorbed by the sample. A heat-sealable tea bag material (available from Dexter Nonwovens, having a place of business in Windsor Locks, Conn., U.S.A., as item #11697) works well for most applications. The bag is formed by folding a 5-inch by 3-inch sample of the bag material in half and heat sealing two of the open edges to form a 2.5-inch by 3-inch rectangular pouch. The heat seals should be about 0.25 inch inside the edge of the material. After the sample is placed in the pouch, the remaining open edge of the pouch is also heat-sealed. Empty bags are also made to be tested with the sample bags as controls. A sample size is chosen such that the teabag does not restrict the swelling of the material, generally with dimensions smaller than the sealed bag area (about 2-inch by 2.5-inch). Three sample bags are tested for each material.

The sealed bags are submerged in a pan of 0.9 percent NaCl solution. After wetting, the samples remain in the solution for 60 minutes, at which time they are removed from the solution and temporarily laid on a non-absorbent flat surface.

The wet bags are then placed into the basket of a suitable centrifuge capable of subjecting the samples to a g-force of 350. (A suitable centrifuge is a HERAEUS LABOFUGE 400, Heraeus Instruments, part number 75008157, available from Heraeus Infosystems GmbH, having a place of business in Hanau, Germany). The bags are centrifuged at a target of 1600 rpm, but within the range of 1500-1900 rpm, for 3 minutes (target g-force of 350). The bags are removed and weighed. The amount of fluid absorbed and retained by the material, taking into account the fluid retained by the bag material alone, is the Centrifuge Retention Capacity of the material, expressed as grams of fluid per gram of material.

Plate Stiffness Test

Stiffness of the composites were measured using the "Zwick Flexibility" test. This test is a measure of stiffness of an article as it is deformed downward into a hole beneath the sample. For the test, the sample is modeled as an infinite plate with thickness t that resides on a flat surface where it is centered over a hole with radius R. A central force applied to the foam directly over the center of the hole deflects the foam down into the hole by a distance w when loaded in the center by a Force F. For a linear elastic material the deflection can be predicted by:

$$w = \frac{3F}{4\pi E t^3}(1-v)(3+v)R^2$$

where E is the effective linear elastic modulus, v is the Poisson's ratio, R is the radius of the hole, and t is the thickness of the foam, taken as the caliper in millimeters measured under a load of about 0.35 kPa, applied by a 7.6 cm diameter Plexiglass platen, with the thickness measured with a Sony U60A Digital Indicator. 30 Taking Poisson's ratio as 0.1 (the solution is not highly sensitive to this parameter, so the inaccuracy due to the assumed value is likely to be minor), we can rewrite the previous equation for w to estimate the effective modulus as a function of the flexibility test results:

$$E \approx \frac{2R^2}{3t^3}\frac{F}{w}$$

The test results are carried out using an MTS ALLIANCE RT/1 testing machine (MTS Systems Corp., Eden Prairie, Minn.) with a 100 N load cell. As an absorbent composite at least 6.25 cm by 6.25 cm square sits centered over a hole of radius 17 mm on a support plate, a blunt probe of 3.15 mm radius descends at a speed of 2.54 mm/min. When the probe tip descends to 1 mm below the plane of the support plate, the test is terminated. The maximum slope in grams of force/mm over any 0.5 mm span during the test is recorded (this maximum slope generally occurs at the end of the stroke). The load cell monitors the applied force and the position of the probe tip relative to the plane of the support plate is also monitored. The peak load is recorded, and E is estimated using the above equation. The bending stiffness per unit width can then be calculated as:

$$S = \frac{Et^3}{12}$$

EXAMPLES

Example 1

Flexible Superabsorbent Binder Polymer Composition

Initiator solutions were prepared as follows: (1) by dissolving 1.04 grams (g) of ascorbic acid in 21.3 g of water; (2) by dissolving 0.5 g of NAPS (sodium persulfate) in 2.9 g of water; and (3) by weighing out 1.93 g of 35% $H_2O_2$.

A crosslinker solution was prepared just prior to initiation. With rapid stirring, 1.4 mL of 3-(trimethoxysilyl)propyl methacrylate (MEMO) were added to 21.3 g of water producing a hazy solution.

A monomer solution was then prepared. While stirring at medium pace with a mechanical stirrer, approximately 626.8 g of water were added into a 1-gallon plastic bucket. To this water, 118.5 g of glacial acrylic acid were added. Then 52.8 g of 0% aqueous NaOH and 31.5 g of polyethylene glycol (PEG) with an average olecular weight of 200 were added and mixed. With continued mixing, this solution mixture was cooled to 20-22° C. while sparging with $N_2$ gas. No cooling water or ice bath was used. When the temperature of the monomer solution reached 20-22° C., the initiation sequence began. To the monomer solution were added the hydrogen peroxide solution, the NAPS solution, 1.16 g of 50% w/w hypophosphorous acid (chain transfer agent), the crosslinker solution, and finally the ascorbic acid solution. The solution was stirred at medium pace with a mechanical stirrer. A thermocouple was used to monitor the temperature and observe the reaction exotherm. When the reaction reached its maximum temperature (approximately 50-55° C.), 212.7 g of water were added to the resulting polymer solution. The polymer solution was allowed to cool while stirring was continued. No cooling water or ice bath was used.

When the polymer solution reached 25-27° C., the remaining 118.5 g of glacial acrylic acid, 52.8 g of 50% aqueous NaOH, and 31.5 g of PEG 200 were added to the solution. This solution mixture was allowed to cool to 25-27° C. while sparging with $N_2$ gas. No cooling water or ice bath was used.

The remaining initiator solutions were prepared as follows: (1) by dissolving 1.04 g of ascorbic acid in 21.3 g of water; (2) by dissolving 0.5 g of NAPS (sodium persulfate) in 2.9 g of water; (3) by weighing out 1.93 g of 35% $H_2O_2$; and (4) by dissolving 1 g of $Fe(SO_4)_3.7H_2O$ in 100 g of water. Then 1.0 g of the 1% $FeSO_4$ solution was added to 5 g of water.

The remaining crosslinker solution was prepared just prior to initiation. With rapid stirring, 1.4 mL of 3-(trimethoxysilyl)propyl methacrylate (MEMO) were added to 21.3 g of water producing a hazy solution.

In this second initiation step, while stirring at medium pace with a mechanical stirrer, the hydrogen peroxide solution, the NAPS solution, 1.16 g of 50% w/w hypophosphorous acid, the crosslinker solution, the diluted iron sulfate solution, and finally the ascorbic acid solution were added to the polymer/monomer solution mixture from above. A thermocouple was used to monitor the temperature and observe the reaction exotherm. The resulting polymer solution was allowed to cool after it reached its maximum temperature. No cooling water or ice bath was used. When the reaction solution reached 30° C., 78.5 g of 50% NaOH solution were added to post-neutralize the superabsorbent polymer solution to a final degree of neutralization of 70%. The resulting polymer solution was stirred approximately 5 minutes after addition of NaOH.

Example 2

Absorbent Composite

A 21 gsm spunbond containing 1.8 denier polypropylene spunbond fibers containing about 1% by weight $TiO_2$ and a wire weave bond pattern which was necked down 25%, and was treated with a surfactant solution mixture to provide wettability. The surfactant can be a 1:3 mixture of GLUCOPON 220 UP (available from Cognis Corporation, having a place of business in Cincinnati, Ohio, U.S.A) and AHCOVEL Base N-62 (available from Uniqema Inc., having a place of business in New Castle, Del., U.S.A.)., and the surfactant add-on level was 0.34% by weight. The spunbond was immersed in the binder solution to thoroughly saturate the fabric. Excess fluid was squeezed out, and the saturated spunbond was dried for 4 minutes at 105° C. in a MATHIS through-air-dryer oven. After drying, the coated fabric had about a 41 gsm dry add-on of the dried flexible superabsorbent binder polymer composition.

The reduction in the stiffness of the absorbent composite was determined utilizing the Plate Stiffness Test described above. As shown in Table 2 below, there is a substantial reduction in stiffness when the absorbent composite is exposed to close-to-the-body conditions of 80% relative humidity compared to the "dried" condition that approximates the condition of the absorbent composite as it is assembled into the absorbent articles and packaged.

TABLE 2

Plate Stiffness* of Absorbent Composite as a Function of Sample Conditioning

| Sample Description 2 pli samples of: | Plate Stiffness (N * mm) as a function of Sample Conditioning | | Percent Reduction at Body Conditions |
|---|---|---|---|
| | Dried 100° C. (10 minutes) | 80% RH (10 minutes) | |
| Uncoated Spunbond 21 gsm | .23 | .25 | — |
| 41 GSM coating on 21 gsm spunbond, 20% PEG content | 2.4 | 0.63 | 81% |

*Values in Table 2 are approximate.

Example 3

Absorbent Article

An absorbent composite was cut from the composite of Example 2 having a length of 101 mm long and 101 mm wide. The absorbent composite was then assembled as an absorbent layer of a pantiliner. The backing sheet of the pantiliner was formed from clear film (available from Pliant Corporation, having a place of business in Chippewa Falls, Wis., U.S.A.). The bodyside liner was an 18.5 gsm polypropylene spunbond with no $TiO_2$ present in the polypropylene. The absorbent composite was placed between the film and the bodyside liner. The liner, film and composite were then joined together using a clear adhesive. The film and bodyside liner were then cut to a square shape, 140 mm by 140 mm. The resulting absorbent article had a central region containing the absorbent and a perimeter region surrounding the central region.

The light transmission of the central region of the absorbent article was tested in accordance with the Light Transmittance Test, and resulted in an average light transmission of 69% (std. dev. 1.3), with an average haze value of 96% (std. dev. 0.6) and a clarity of 44% (std. dev. 7.8). The light transmission of the perimeter region of the absorbent article was also tested and resulted in an average light transmission of 84% (std. dev. 2.5), with an average haze value of 68.1.5% (std. dev. 6.2) and a clarity of 74.3% (std. dev. 2.2).

Example 4

Absorbent Article

Another absorbent article was prepared using the absorbent composite of Example 2. In this example, two of the absorbent composites, each having a length of 101 mm long and 101 mm wide, were place on top of each other. The 2-layer absorbent composite was then placed between the film and the bodyside liner described in Example 2 above. The liner, film and composite were then joined together using a clear adhesive. The film and bodyside liner were then cut into a square shape, 140 mm by 140 mm. The resulting absorbent article had a central region containing the 2-layer absorbent composite and a perimeter region surrounding the central region.

The light transmission of the central region of the absorbent article was tested in accordance with the Light Transmittance Test, and resulted in an average light transmission of 55.3% (std. dev. 5.3), with an average haze value of 98.2% (std. dev. 0.1) and a clarity of 14.1% (std. dev. 1.4). The light transmission of the perimeter region of the absorbent article was also tested and resulted in average light transmission of 84% (std. dev. 2.6), with an average haze value of 67% (std. dev. 4.8 ) and a clarity of 75% (std. dev. 1.7).

It will be appreciated that details of the foregoing examples, given for purposes of illustration, are not to be construed as limiting the scope of this invention. Although only a few exemplary embodiments of this invention have been described in detail above, those skilled in the art will readily appreciate that many modifications are possible in the examples without materially departing from the novel teachings and advantages of this invention. For example, features described in relation to one example may be incorporated into any other example of the invention.

Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention. As various changes could be made in the above constructions without departing from the scope of the invention, it is intended that all matter contained in the above description shall be interpreted as illustrative and not in a limiting sense.

The invention claimed is:

1. A translucent absorbent article comprising a backing layer and an absorbent layer;
   wherein the absorbent layer is positioned adjacent the backing layer;
   wherein the absorbent layer comprises a substrate and a flexible superabsorbent binder polymer composition applied to the substrate;
   wherein the flexible superabsorbent binder polymer composition comprises the reaction product of:
   at least 15% by mass monoethylenically unsaturated monomer selected from carboxylic acid, carboxylic acid salts, sulphonic acid, sulphonic acid salts, phosphoric acid, and phosphoric acid salts;
   a plasticizer;
   an acrylate or methacrylate ester that contains an alkoxysilane functionality;
   a chain transfer agent;
   a transition metal salt;
   an initiator system; and
   a neutralizing agent;
   wherein the flexible superabsorbent binder polymer composition has a weight average molecular weight of from about 100,000 to about 650,000 g/mole;
   wherein the flexible superabsorbent binder polymer composition has a viscosity after 16 hours of less than about 10,000 cps;
   wherein the flexible superabsorbent binder polymer composition has a residual monoethylenically unsaturated monomer content of less than about 1000 ppm;
   wherein the absorbent layer has a light transmittance of at least 45% and the backing layer has a light transmittance of at least 60%; and
   wherein in the absorbent article has a minimum light transmittance of at least 45%.

2. The translucent absorbent article of claim 1, wherein the plasticizer is a polyethylene glycol.

3. The translucent absorbent article of claim 1, wherein the absorbent article has a perimeter region and a central region, the backing layer is present in both the perimeter region and the central region, and the absorbent layer is positioned on the backing layer and in the central region of the absorbent article.

4. The translucent absorbent article of claim 3, wherein the perimeter region of the absorbent article has a light transmittance of at least 60% and the central region of the absorbent article has a light transmittance of at least 45%.

5. The translucent absorbent article of claim 4, wherein the perimeter region of the absorbent article has a light transmittance of at least 80% and the central region of the absorbent article has a light transmittance of between about 55% and about 79%.

6. The translucent absorbent article of claim 1, further comprising a liner layer, wherein the liner layer is positioned in the absorbent article such that the absorbent layer is positioned between the liner layer and the backing layer, wherein the liner layer has a light transmittance of at least 60%.

7. The translucent absorbent article of claim 6, wherein the absorbent article has a perimeter region and a central region, the backing layer and the bodyside liner are each present in both the perimeter region and the central region, and the absorbent layer is positioned between the bodyside liner and the backing layer only in the central region of the absorbent article.

8. The translucent absorbent article of claim 1, wherein the absorbent layer has an overall thickness of between about 0.25 mm to about 5.0 mm.

9. The translucent absorbent article of claim 8, wherein the absorbent layer has an overall thickness of between about 0.25 mm to about 1.5 mm.

10. The translucent absorbent article of claim 1, further comprising a garment attachment adhesive applied to a side of the backing layer opposite the absorbent layer, wherein the garment attachment adhesive has a light transmittance of at least 60%.

11. The translucent absorbent article of claim 10, wherein the garment attachment adhesive has a light transmittance of at least 80%.

12. The translucent absorbent article of claim 10, further comprising a peel strip attached to the garment adhesive, wherein the peel strip has a light transmittance of at least 60%.

13. The translucent absorbent article of claim 12, wherein the peel strip has a light transmittance of at least 80%.

14. The translucent absorbent article of claim 1 further comprising flaps, wherein the flaps have a light transmittance of at least 45%.

15. The translucent absorbent article of claim 14 further comprising a body contacting surface, a surface opposed the body contacting surface, and longitudinal edges extending along an edge of the absorbent article, wherein the absorbent layer is positioned between the body contacting surface and the surface opposed the body contacting surface, and wherein the flaps extend from the longitudinal edges of the absorbent article.

* * * * *

UNITED STATES PATENT AND TRADEMARK OFFICE
CERTIFICATE OF CORRECTION

PATENT NO.        : 7,619,131 B2                                    Page 1 of 1
APPLICATION NO.   : 11/292570
DATED             : November 17, 2009
INVENTOR(S)       : Dave Allen Soerens It is certified that error appears in the above-identified patent and that said Letters Patent is hereby corrected as shown below:

(*) Notice: should read, Subject to any disclaimer, the term of this patent is extended or adjusted under 35 U.S.C. 154 (b) by 693 days.

Signed and Sealed this

Tenth Day of August, 2010

David J. Kappos
*Director of the United States Patent and Trademark Office*